United States Patent
Hamada et al.

(10) Patent No.: US 9,424,642 B2
(45) Date of Patent: Aug. 23, 2016

(54) EXTRACTION OF MYOCARDIAL CONTOUR POINTS

(71) Applicant: Nihon Medi-Physics Co., Ltd., Tokyo (JP)

(72) Inventors: Kazuo Hamada, Tokyo (JP); Kazunori Kobayashi, Tokyo (JP)

(73) Assignee: Nihon Medi-Physics Co., Ltd., Tokyo (JP)

( * ) Notice: Subject to any disclaimer, the term of this patent is extended or adjusted under 35 U.S.C. 154(b) by 121 days.

(21) Appl. No.: 14/469,709

(22) Filed: Aug. 27, 2014

(65) Prior Publication Data

US 2015/0063670 A1    Mar. 5, 2015

(30) Foreign Application Priority Data

Aug. 29, 2013   (JP) .................................. 2013-177564

(51) Int. Cl.
| | | |
|---|---|---|
| *G06T 7/00* | (2006.01) | |
| *A61B 6/00* | (2006.01) | |
| *G06T 11/00* | (2006.01) | |
| *A61B 6/03* | (2006.01) | |
| *A61B 5/00* | (2006.01) | |
| *A61B 5/055* | (2006.01) | |

(52) U.S. Cl.
CPC ............ *G06T 7/0012* (2013.01); *A61B 6/037* (2013.01); *A61B 6/503* (2013.01); *A61B 6/5217* (2013.01); *A61B 6/5235* (2013.01); *G06T 7/0083* (2013.01); *G06T 11/008* (2013.01); *A61B 5/0044* (2013.01); *A61B 5/055* (2013.01); *G06T 2200/04* (2013.01); *G06T 2207/10076* (2013.01); *G06T 2207/10104* (2013.01); *G06T 2207/10108* (2013.01); *G06T 2207/30048* (2013.01)

(58) Field of Classification Search
None
See application file for complete search history.

(56) References Cited

U.S. PATENT DOCUMENTS

| | | | | |
|---|---|---|---|---|
| 5,797,396 A | * | 8/1998 | Geiser | ..................... G06T 7/602 382/128 |
| 7,693,563 B2 | * | 4/2010 | Suresh | ................ G06F 19/3437 382/128 |
| 2012/0101368 A1 | * | 4/2012 | Masumoto | ............. A61B 6/503 600/420 |
| 2012/0263368 A1 | * | 10/2012 | Nakano | .................. A61B 6/032 382/133 |

FOREIGN PATENT DOCUMENTS

| | | |
|---|---|---|
| JP | 2014-1185991 A | 10/2014 |
| WO | WO 2013/047496 A1 | 4/2013 |

\* cited by examiner

*Primary Examiner* — Jon Chang
(74) *Attorney, Agent, or Firm* — Harrington & Smith

(57) ABSTRACT

One of the preferred embodiments includes: (a) creating a summed 3D nuclear medicine imaging data by summing a plurality of 3D nuclear medicine imaging data pixel by pixel; (b) determining pixels corresponding to myocardial regions in the summed 3D nuclear medicine imaging data; (c) defining a plurality of tracing directions based on the summed 3D nuclear medicine imaging data, and determining a reference myocardial center base point, a reference inner myocardial wall base point and a reference outer myocardial wall base point for each of the tracing directions; (d) determining a phase-specific myocardial center base point for each of the tracing directions for each of the phases; and (e) seeking a difference between the reference myocardial center base point and the phase-specific myocardial center base point, and determining a phase-specific inner myocardial wall base point and a phase-specific outer myocardial wall base point.

24 Claims, 30 Drawing Sheets (a)

(b)

(c)

EXTRACTION OF MYOCARDIAL CONTOUR POINTS

FIELD

What are disclosed in the present application is generally related with extraction of myocardial contour points from a myocardial nuclear medicine image.

BACKGROUND

The nuclear medicine imaging such as SPECT (Single Photon Emission Tomography) or PET (Positron Emission Tomography) is a technology for imaging comprising injecting radiopharmaceuticals in a human body, acquiring gamma-rays emitted due to decays of radioactive nuclide by a detector, and reconstructing the acquired data to image data. CT and MRI, which are different types of bio-imaging technologies, are used mainly for investigating abnormalities of morphologies of body tissues. On the other hand, the nuclear medicine imaging technologies can be used not only for investigating morphologies, but also for investigating statuses of functions or metabolisms of internal organs or tissues, based on information such as distributions, aggregations, or time-dependent changes of the injected radiopharmaceuticals, i.e., numbers of counts of the gamma-rays acquired by the detector.

One of the application areas of the nuclear medicine imaging technologies is the myocardial perfusion imaging. The myocardial perfusion imaging (MPI) can be practiced by using SPECT. This method uses radiopharmaceuticals having the nature of being ingested into cardiomyocytes in proportion to the amount of blood flow of the coronary artery as a tracer. Such radiopharmaceuticals may be $^{201}$TlCl or $^{99m}$Tc-tetrofosmin. After such tracer is injected to a subject, the SPECT system acquires gamma-rays generated from the tracer and reconstructs images from the acquired gamma-rays. In these images, locations of ischemia can be appeared as dark sites. So it is possible to investigate whether there are ischemia in, e.g., a cardiac muscle, or not. The Investigation of locations of ischemia in a cardiac muscle is very useful for diagnosing of a myocardial infarction (MI) and an angina pectoris (AP), and identifying locations of lesions caused by ischemia. Since the heart is a moving organ, the SPECT acquisition generally involves gating by electrocardiogram (ECG) for acquiring gamma-rays. Such type of SPECT myocardial imaging has been called as an ECG-gated myocardial SPECT imaging. Usually, the cardiac muscle of the left ventricle is a target for imaging in the ECG-gated myocardial SPECT imaging.

One of the technical challenges in the ECG-gated myocardial SPECT imaging is how to identify the myocardial regions in the reconstructed images. One of the solutions is to manually mark contours of region which may correspond to myocardium based on visual observation in each image slice. But this method has a disadvantage of requiring too much time. So there are prior developments of software for extracting contour points of the myocardial region. QGS (Quantitative Gated SPECT) is one of such software. It was developed by Cedars-Sinai Medical Center. Emory Cardiac Toolbox is also one of such software. It was developed by Emory University. pFAST, developed by Sapporo Medical University, is also such software. The applicant of the present application also disclosed sophisticated algorithms for automatic extraction of myocardial contour points in WO2013/047496 and JP patent application No. 2013-062441.

Prior art document: WO2013/047496

SUMMARY

However, conventional methods for automatic myocardial contour extraction analyze images obtained in only a specific phase of the cardiac cycle. Or, the other types of conventional methods analyze images reconstructed by data acquired continuously without considering cardiac phase cycle (i.e., acquired without ECG gating). In other words, the conventional methods do not take into account the positional relationships of cardiac muscles between different cardiac phase cycle in the contour extractions. The conventional methods do not take into account the move of the cardiac muscles in the contour extractions. So when an operator compares myocardial images extracted in different phases, the operator may feel that changes of myocardial contours in different phases are not natural.

The present invention was created for overcoming such problem and for providing a technology for myocardial contour extraction in which changes of extracted myocardial contours in phases can be smoother than conventional technologies.

Preferred embodiments of the present invention include:

(a) creating a summed 3D nuclear medicine imaging data by summing a plurality of 3D nuclear medicine imaging data pixel by pixel, wherein each of the plurality of 3D nuclear medicine imaging data is associated with a different phase of a cardiac cycle;

(b) determining pixels corresponding to myocardial regions in the summed 3D nuclear medicine imaging data;

(c) defining a plurality of tracing directions based on the summed 3D nuclear medicine imaging data, and determining a reference myocardial center base point, a reference inner myocardial wall base point and a reference outer myocardial wall base point for each of the tracing directions;

(d) determining a phase-specific myocardial center base point for each of the tracing directions for each of the phases based on the corresponding 3D nuclear medicine imaging data; and (e) seeking a difference between the reference myocardial center base point and the phase-specific myocardial center base point, and determining a phase-specific inner myocardial wall base point and a phase-specific outer myocardial wall base point by shifting the reference inner myocardial wall base point and the reference outer myocardial wall base point respectively based on the determined difference, for each of the tracing directions for each phase.

The preferred embodiments of the present invention have a feature of determining the phase-specific inner myocardial wall base points and the phase-specific outer myocardial wall base points based on the reference myocardial center base points, the reference inner myocardial wall base point and the reference outer myocardial wall base point which are determined by the summed 3D nuclear medicine imaging data. This feature provides an advantage of making the positional changes of the determined phase-specific myocardial wall base points smoother in phases. In another words, the preferred embodiments of the present invention provide an advantage that the shape change of the myocardial contour between the phases can be more natural than the cases in the existing technologies.

According to some embodiments, said creating a summed 3D nuclear medicine imaging data in said step (a) may be performed after applying position adjustments for at least some of said 3D nuclear medicine imaging data.

By summing phase-specific 3D nuclear medicine imaging data after applying position adjustment processing, it is possible to reduce the blur of the myocardial contours in the summed image.

According to some embodiments, said step (c) may comprise:
   creating a binary image data by assigning a first value to pixels in the summed 3D nuclear medicine imaging data which are determined as being associated with myocardial regions, and assigning a second value to pixels in the summed 3D nuclear medicine imaging data which are determined as not being associated with myocardial regions; and
   determining the reference myocardial center base point, the reference inner myocardial wall base point and the reference outer myocardial wall base point based on said binary image data in each of the tracing directions.

By employing the binary image data, the determinations of myocardial contours can be easier, and thus the determination of the reference myocardial center base points, the reference inner myocardial wall base points and the reference outer myocardial wall base points can be easier.

According to some embodiments, said plurality of tracing directions defined in said step (c) may be defined such that:
   for a region located apical side, the tracing directions are defined as radially and three-dimensionally from a predetermined starting point in a cardiac ventricle;
   for a region located basal side, the tracing directions are also defined as radially and three-dimensionally from a different starting point in a cardiac ventricle; and
   for a central myocardial region located between the region located apical side and the region located basal side, the tracing directions are defined as radially and two-dimensionally in a short axial plane.

The inventors of the present application have found that defining the tracing directions as such can improve a quality of myocardial contour extraction.

According to some embodiments, said step (d) may be performed such that the phase-specific myocardial center base point may be determined based not only on the 3D nuclear medicine imaging data of the corresponding phase, but also on the 3D nuclear medicine imaging data of the neighboring phases.

By taking data of the neighboring phases into account, the shape change of the extracted myocardial contour between phases can be smoother.

According to some embodiments, inter-slice corrections and/or intra-slice corrections may be applied to positions of at least some of the phase-specific myocardial center base points, before determining the phase-specific inner myocardial wall base points and phase-specific outer myocardial wall base points. Such correction processing can improve quality of myocardial contour extractions.

According to some embodiments, inter-phase corrections may be applied to positions of at least some of the phase-specific myocardial center base points, before determining the phase-specific inner myocardial wall base points and phase-specific outer myocardial wall base points. Such correction processing may improve smoothness of position changes in phase of the extracted myocardial contours.

According to some embodiments, inner myocardial wall points and outer myocardial wall points may be determined for whole of the 3D nuclear medicine imaging data phase by phase based on the corresponding phase-specific inner myocardial wall base points and the corresponding phase-specific outer myocardial wall base points.

The embodiment of the present inventions may be methods, apparatuses, computer programs, and etc which involve at least one of the above-mentioned processes.

Concrete examples of the above-mentioned processes will be explained later.

The claim section of the present application defines some constructions which the applicant wishes to obtain patent protections in respective claims. However, it should be noted that the applicant may seek patent protections for any novel technical features which can be understood from the attached description and/or the drawings in future, even though they may not be written in the claim section now.

EXPLANATIONS OF PREFERRED EMBODIMENTS

Preferred embodiments of the present invention will now be explained below with reference to the attached drawings.

Figure 1A:
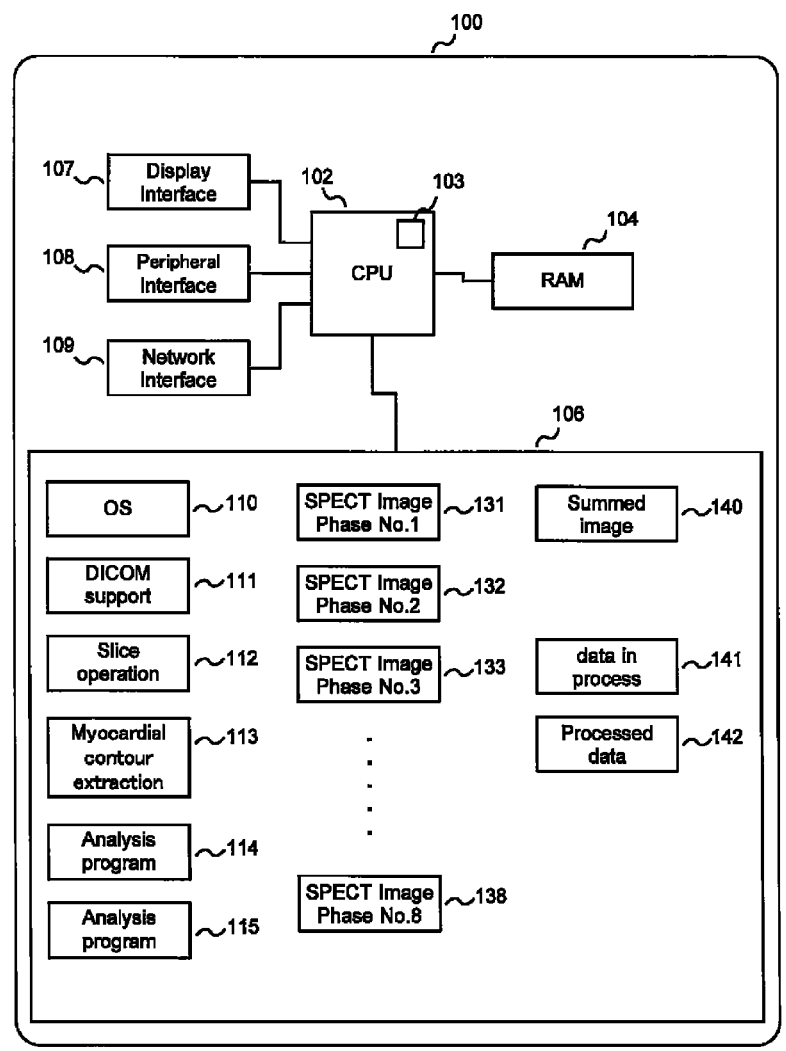
FIG. 1A: a diagram for explaining a construction of an apparatus or a system 100 for performing various processes disclosed in the present application.

FIG. 1A: a diagram for explaining a construction of a system 100 for performing various processes disclosed in the present application. As illustrated in FIG. 1A, the hardware configuration of the system 100 can also be seen in conventional computers. As similar to the conventional computers, the system 100 may comprise CPU 102, main memory 104, auxiliary storage 106, display interface 107, peripheral interface 108, network interface 109, and so on. CPU 102 may comprise cache memory 103 that is faster than main memory 104. System 100 may be configured as an apparatus which accommodate most of its components in a single housing, or an arrangement comprised by a plurality of physically-different housings. Similarly to conventional computers, the main memory 104 may comprise a fast memory such as RAM (random access memory), and the auxiliary storage 106 may comprise a cheap and a large capacity storage such as a hard disk, a flash memory, and a SSD. According to some embodiments, the auxiliary storage 106 may comprise a plurality of physically different storages. According to some embodiments, the auxiliary storage 106 may be configured as a system implemented in an housing that is physically different from the housing of system 100 and connected to the system 100 by an appropriate interface. A display device may be connected to the system 100 via display interface 107 for displaying information. User interface devices may also be connected to the system 100 via peripheral interface 108 for inputting information. Such user interface devices may comprise a keyboard, a mouse, and/or a touch panel. The peripheral interface 108 may be a USB interface. The network interface 109 can be used for connecting to the other computers or Internet via a network. The most fundamental functions of system 100 are provided by an operating system 110 stored in auxiliary storage 106 by being loaded and executed by CPU 102. And functions which are not provided by the operating system 110 are provided by various programs stored in auxiliary storage 106 by being loaded and executed by CPU 102.

The apparatus or system 100 of the illustrated embodiment may comprise DICOM support program 111, slice operation program 112, myocardial contour extraction program 113. DICOM support program 111 is a program for supporting DICOM, which has practicality been a standard for the file format and the communication rules for the medical imaging data. The myocardial nuclear medicine image data subjected to the myocardial contour extraction process of the presented embodiments may have a file format compatible to DICOM, and its inputting, outputting, or saving the myocardial nuclear medicine image data may be supported by DICOM support program 111. Slice operation program 112 provides re-slicing functions for, for example, cutting the 3D myocardial nuclear medicine image data at a desired cross-section and creating a 2D slice image. Programs having such functions have already been available in the market and installed in a lot of workstations for handling medical images. So it is possible to implement DICOM support program 111 and slice operation program 112 easily by utilizing existing technologies.

Myocardial contour extraction program 113 is the most important element for providing the automatic extraction of myocardial contours provided by the illustrated embodiments. The various processes disclosed in the present application may be implemented by program codes of a whole of or a part of the myocardial contour extraction program 113 being loaded and executed by CPU 102. In each process, CPU 102 may load data from a storage device and perform operations, and store a resulting data to cache memory 103 or main memory 104, in accordance, for example, with the instructions of the myocardial contour extraction program 113. The stored data may be used for further processing in accordance with instructions of the myocardial contour extraction program 113, and/or stored in the auxiliary storage 106. Auxiliary storage 106 may be used for storing, e.g., 3D myocardial SPECT image data 131-138, data 141 that is created during the process, date 140 or 142 which are created by completions of the processes, and so on. Cache memory 103 and main memory 104 may also be used for storing data to be processed temporary. In any processes presented in this description, data or results of calculations may be exchanged similarly between CPU 102 and memory devices such as device 103, 104, and/or 106.

According to some embodiments, the apparatus or the system 100 may comprise programs for performing different types of analysis using the results of myocardial contour extractions by the myocardial contour extraction program 113. The illustrated embodiments comprises programs 114 and 115 as such analysis programs. They may be stored in the auxiliary storage 106, for example.

Myocardial contour extraction program 113 and/or analysis programs 114, 115 may be implemented as a single executable file, or as a set of programs comprised by a plurality of executable files. Myocardial contour extraction program 113 and/or analysis programs 114, 115 may be enabled to call DICOM support program 111 and use. For example, myocardial nuclear medicine image 113 and/or analysis programs 114, 115 may be configured to call and use DICOM support program 111 so that it can load the myocardial nuclear medicine image data and save the processing results in the DICOM format. Similarly, myocardial contour extraction program 113 and/or analysis programs 114, 115 may be enabled to call slice operation program 112 and use. For example, myocardial nuclear medicine image 113 and/or analysis programs 114, 115 may be configured obtain a 2D image data of a short-axis image and/or a 2D image data of a long-axis image by calling and using slice operation program 112. In some embodiments, myocardial contour extraction program 113 and/or analysis programs 114, 115 may be configured as a program having functions of DICOM support program 111 and/or slice operation program 112. There are various ways for programming. So it should be noted that the examples presented in the descriptions and/or the drawings of the present application do not add any limitations to the ways of programming the programs 113, 114, and 115.

In some embodiments, a part of the processing of the above-mentioned programs may be implemented by a programmable logic or a dedicated hardware circuit. Such embodiments are also included in the scope of the present invention.

FIG. 1A illustrates that all of the operating system 100, myocardial contour extraction program 113, image data 131, and the other data and programs are stored in the same auxiliary storage 106. But in the other embodiments, one or more of these data and programs may be stored in a physically different storage. For example, in some embodiments, myocardial contour extraction program 113 and/or analysis programs 114, 115 may be stored in a optical disc such as CD-ROM or DVD-ROM. These programs may be provided and sold as different elements from system 100, in the form of, for example, being stored in a storage media such as an optical media or a USB memory which is easy to carry. These programs may be provided and sold in the form of downloading via a network.

Storage 106 may store a plurality of data which are subjected to the processes of myocardial contour extraction program 113 and/or analysis programs 114, 115. FIG. 1A illustrates eight 3D SPECT image data 131-138 as an example (image data 134-137 are illustrated by the abbreviated form). For example, each of these eight image data was created from a SPECT measurement for the same single subject. But each of these eight image was created based on data acquired at a different phase of the cardiac cycle. So these 3D SPECT image (data) 131-138 may be called as phase image (data) in this description. Hence, the set of these eight SPECT image data represent a set of data for a whole of the cardiac cycle. Please note that the number of 3D SPECT image data included in one set of data representing a whole of the cardiac cycle may be a different number such as 4 and 17, where each of the 3D SPECT image data corresponds to a different phase of the cardiac cycle.

The system or apparatus 100 may comprise a power supply and a cooling system in addition to elements illustrated in FIG. 1A, in a similar way as conventional computers. The processing means 102 may be realized as a single CPU or multiple CPUs. The processing means 102 may be realized by multiple CPUs stored in physically different housings respectively and connected each other via some interfaces or networks. The processing means 102 may be realized by a virtualization technology. The processing means 104 and 106 may also be realized by a single storage device, a plurality of storage devices, a plurality of storage devices store in different housings respectively and connected each other via an interface or a network, or a virtualization technology. The computer systems embodying the present invention can employ any configurations. The scope of the present invention is never limited by the configurations of the computer systems. Generally, the present invention can be embodied as (1) a program comprising instructions configured to cause an apparatus or a system, when being executed by processing meas of the apparatus or the system, to carry out processes disclosed in the present application; (2) a method of operations of an apparatus or a system realized by said program being executed by said processing means; (3) an apparatus or a system comprising said program and a processing means enabled to execute said program; and so on. And the program embodying the present application can be stored in a media such as DVD-ROM for selling. The program embodying the present application can be sold by means of downloading via a network.

Figure 1B:
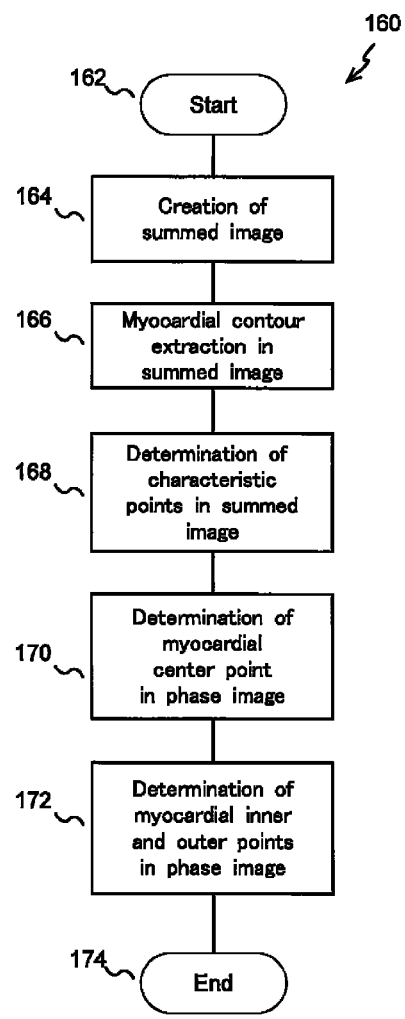
FIG. 1B: a flow chart for explaining a basic flow for various myocardial contour extraction processes presented as examples in the present application.

FIG. 1B is a flow chart for explaining a basic flow of the myocardial contour extraction process 160 presented as an example in the present application. Step 162 indicates a start of the process. In step 164, a summed 3D nuclear medicine imaging data is created by summing several 3D nuclear medicine imaging data (for example, image data 131-138) pixel by pixel. Each of these 3D nuclear medicine imaging data to be summed may be associated with a different phase of a cardiac cycle. Hereinafter the summed 3D nuclear medicine imaging data may be expressed simply as a summed image or a summed image data. The summation calculation performed in this step can be expressed as the following formula.

$$Vs_{ijk} = \sum_{p=1}^{n} Vp_{ijk} \qquad \text{[Formula 1]}$$

Here, $Vp_{ijk}$ expresses a pixel value of a pixel located at i-th in x direction, j-th in y direction, and k-th in z direction (meaning of i-th, j-th and k-th will also be the same in the following texts) of the 3D nuclear medicine imaging data corresponding to phase p (p=1~n), and $Vs_{ijk}$ expresses a pixel value of a pixel located as i-th, j-th, and k-th of the summed image data.

Before performing the above-mentioned summation, it would be preferable that the relative positions of the myocardium in respective 3D SPECT image data have been adjusted so that they can be the same. If the relative positions of myocardium are not the same among the 3D SPECT image data of different phases, the contours of myocardium in the summed image may become undesirably blurred. So it is preferable to apply position matching processing if the relative positions of the myocardium in respective images are not the same. An examples of the position matching algorithm will be presented later.

It should be noted that the value of $Vs_{ijk}$ may exceed the dynamic range of the summed 3D nuclear medicine imaging data. So it may be preferable to adjust the value of $Vs_{ijk}$ by dividing it by an appropriate value to avoid any pixels of the summed image data exceeding the dynamic range. For example, if the dynamic range of the summed image data is eight bit, it may be preferable to apply a division by Vmax/255 to the pixel value (i.e., $Vs_{ijk}$) of each pixel of the summed image data, where Vmax expresses the maximum pixel value of the raw summed image data.

In step 166, pixels corresponding to myocardial regions are determined in the summed 3D nuclear medicine imaging data. The determination of the myocardial regions can be performed by any conventional methods. For example, it is possible to use algorithms which the applicant disclosed in WO2013/047496 or JP patent application No. 2013-062441. Or, it is possible to use the other existing technologies mentioned in the background portion of this description for contour extraction.

In step 168, characteristic points regarding the myocardium are determined in the summed 3D nuclear medicine imaging data. In this step, a plurality of tracing directions are defined based on the summed 3D nuclear medicine imaging data. And then a reference myocardial center base point, a reference inner myocardial wall base point and a reference outer myocardial wall base point are determined for each of the tracing directions. The details of processes will be explained later.

In step 170, characteristic points regarding the myocardium are determined in each of the 3D nuclear medicine imaging data corresponding to different phases of a cardiac cycle (for example, image data 131-138). In this step, a reference myocardial center base point is determined for each of the tracing directions (which are defined in the summed image data as mentioned above) for each of the phase images data. The reference myocardial center base points in each of the individual phases are determined based on at least the corresponding phase image data. The details of processes will be explained later.

In step 172, inner myocardial wall base points and outer myocardial wall base points are determined for each phase image data. The inner- and outer-myocardial wall base points are determined for each of said tracing directions, which have been defined for the summed image data. In this step, a difference between a reference myocardial center base point determined in the summed image data and a myocardial center base point determined in an individual phase image data is calculated for each of said tracing directions. And then an inner myocardial wall base point and an outer myocardial wall base point are determined for each of said tracing directions for said individual phase image data by shifting the inner myocardial wall base point and the outer myocardial wall base point determined in the summed image data at the corresponding tracing direction. The details of processes will be explained later.

Step 174 indicates the end of the process.

Further details of the steps in FIG. 1B will now be explained.

<Image Data Subjected to the Processing>

On top of the further detail explanations, the image data to be processed in the embodiments presented in the present application will be explained a bit more. The image data to be processed in the myocardial contour extraction process according to the presented embodiments are 3D nuclear medicine imaging data obtained by the nuclear medical technologies such as SPECT or PET. In principle, the nuclear medicine imaging data are obtained by acquiring gamma rays generated from decays of radioactive tracers injected to a subject, and transforming counting data of the gamma rays to an image. Therefore, each pixel of nuclear medicine imaging data has a pixel value relating to the number of counts of gamma rays emitted from a region of the subject corresponding to the pixel. So the pixel value of the pixel of the image data may be called as 'count value', 'count number', 'count', 'count data', and so on. However, please note that the pixel values may not be integer numbers, because of results of interpolations and/or normalizations.

The image data to be processed in the myocardial contour extraction process of the presented embodiments may be a set of 3D nuclear medicine imaging data obtained by ECG-gated myocardial SPECT imaging technique. Such image data may be the set of image data 131-138 mentioned above and illustrated in FIG. 1A. Each of these SPECT imaging data was created from radiation count data obtained from a specific phase of a cardiac cycle. That is, each of these SPECT imaging data was created from gamma-ray counts measured at a predetermined time passed from a gate defined based on ECG and in a predetermined time window. As mentioned, the image data 131-138 may be called as phase images or phase image data since they are associated with respective unique phases.

<Step 164—Creation of Summed Image Data>

Figure 2A:
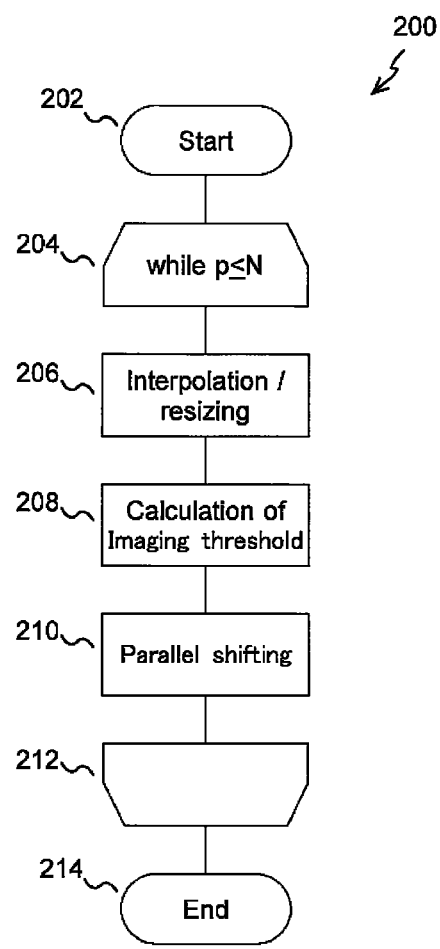
FIG. 2A: a flow chart for explaining a position adjustment process applied, according to an example embodiment, to 3D nuclear medicine imaging data which are subjected to the myocardial contour extraction process in the disclosed examples.
Figure 2B:
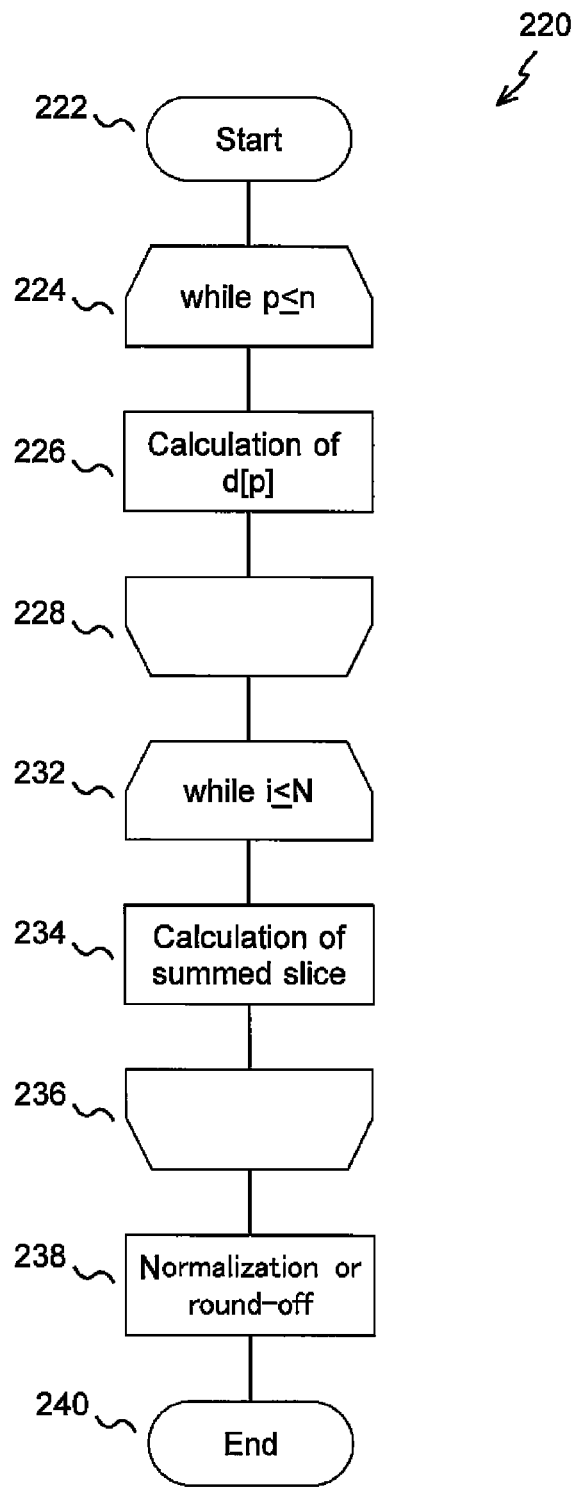
FIG. 2B: a flow chart for explaining a process for creating a summed image data in the disclosed examples.

FIGS. 2A and 2B are flow charts for explaining an example process applicable to step 164 of FIG. 1. It should be noted that the present steps are merely examples. It should be understood that all the steps shown in FIGS. 2A and 2B may not be mandatory for step 164 of FIG. 1. In some embodiments, one or more of the steps in FIGS. 2A and 2B may not be implemented. It should also be understood that the order of the presented steps are not mandatory. In some embodiments, these steps may be performed in different orders. Some steps may be performed in parallel. Some steps may be combined and performed integrally. There are many available variations for implementing the presented steps. And it is the same for all the steps in the processes disclosed in the present application. Each of the example steps of the example processes may be performed by CPU 102 when it executes at least a part of the instructions of the myocardial contour extraction program 113. At least a part of the instructions of myocardial contour extraction program 113 may be configured to operate CPU 102 to call and use DICOM support program 111 and/or slice operation program 112 for performing some processes.

Process 200 illustrated in FIG. 2A is an example process for matching relative positions of myocardia among the 3D nuclear medicine imaging data (for example, phase image data 131-138), which are the targets of the myocardial contour extraction process of the presented embodiments.

Step 202 indicates a start of the process. The loop defined by steps 204 and 212 indicates that the same process is applied to all of the phase image data subjected to the myocardial contour extraction process of the presented embodiments. In step 204, p indicates an identifier (or a phase number) of a particular one of the phase image data. The p varies from 1 to N, which is the number of phase image data in a cardiac cycle. For example, if the set of image data 131-138 constructs a data for one cardiac cycle, then N=8.

In step 206, numbers of pixels or sizes of pixels of respective image data 131-138 may be changed. The most frequently used numbers of pixels of 3D image data created by the market available SPECT system is 64*64 pixels or 128*128 pixels per a short axis slice. There is no standard number for the number of short axis slices, i.e., a resolution along the long axis. So different system may have a different value. So the actual size corresponding to each pixel is different depending on the system. In step 206, the number of pixels and/or the size of each pixel of one or more of image data 131-138 may be changed to the desired values, by applying, for example, a resizing process based on, e.g., a triple linear interpolation process. For example, the number of pixels and the size of each pixel of image data 131-138 may be adjusted in this step to 128*128 pixels per a short axis slice, and 2 mm for all of the axial, coronal, and sagittal directions. During the adjustment, the pixel values which are greater than a threshold or smaller than a different threshold may be changed to predetermined values. For example, some pixels may have negative pixel values because of an interpolation process. Such pixel values may be reset to zero.

In step 208, a special value so called 'imaging threshold' is defined for subsequent steps. This value is defined by the following formula.

Imaging threshold={(maximum count value−minimum count value)*threshold coefficient}−minimum count value    [Formula 2]

Here, the maximum count value and the minimum count value may be calculated based on a pixel region where most of the tissues corresponding to this region would be myocardia. For example, the maximum count value may be the maximum pixel value in the region comprised by upper half of all the short axis slices. Similarly, the minimum count value may be the minimum pixel value in the region comprised by upper half of all the short axis slices. Please note that the orientation of the body tissues in the short axis slices in the field of nuclear medicine imaging are practically standardized such that the myocardium locates the upper half of the image of the slice, and the liver or the intestinal canals locates the lower half of the image of the slice. Therefore, the maximum count value and the minimum count value calculated based on the upper half of the pixels of the short axis slices would reflect the count values of regions where the most of the imaged tissues are myocardial cells. The user can set the threshold coefficient in the formula 2 arbitrarily. Myocardial contour extraction program 113 may be configured to receive an input via peripheral interface 108 for setting the threshold coefficient.

In some embodiments, the imaging threshold defined in the formula 2 is used for several different processes. And the threshold coefficients and the regions of pixels or slices for calculating the imaging thresholds may be different for respective processes. In some embodiments, several different imaging thresholds may be calculated in step 208 with different threshold coefficients and/or regions of pixels or slices. The calculated threshold coefficients may be stored in RAM 104 or auxiliary storage 106 so that they can be called and used for later stages.

In step 210, an image center is calculated, which is an average coordinate of all pixels of the current one of image data 131-138 in the loop 204-212. In this step, an image centroid is also calculated, which is an average coordinate of all pixels having count values greater than said imaging threshold, for the current one of image data 131-138 in the loop 204-212. Then, a distance between the image center and the image centroid is calculated, and checked whether the calculated distance is longer than one of the vertical-, horizontal-, and depth-length of the corresponding image data multiplied by a predetermined percentage. If it is longer, then a parallel shift operation is performed for each of the pixels of the corresponding image data so that the position of the image center can be the same as the position of the image centroid.

According to the study of the inventor, the threshold coefficient for calculating the imaging threshold used in step 210 may preferably be around 30% for good results in the myocardial contour extraction. And according to the study of the inventor, the predetermined percentage mentioned above may preferably be around 10% for good results in the myocardial contour extraction.

In some embodiments, the process illustrated by steps 206-210 may have already applied to the image data 131-138. That is, the image data 131-138 store in the auxiliary storage 106 may be the ones to which the process of steps 206-210 has already been applied. In such cases, the process of steps 206-210 is of course not needed to be performed again.

After processing all the phase data, the process exits from the loop 204-212. Step 214 indicates the end of the process.

FIG. 2B is a flow chart for explaining the process 200 which is to create a summed image data by summing the phase image data.

Step 222 indicates a start of the process. The process performed in the loop defined by steps 224 and 228 is to calculate a difference of No. of slices, between the slice in which the image centroid exists in a particular phase image data (e.g., the phase image data corresponding to the phase No. 1), and the slice in which the image centroid exists in the other phase data (e.g., the phase image data corresponding to the phase No. n). For example, if the image centroid exists in slice No. 100 in the phase image corresponding to phase No. 1 and if the image centroid exists in slice No. 110 in the phase image corresponding to phase No. 2, the difference calculated in this loop for p=2 will be 10. Here, the term 'slice' means a slice containing a short axis image. As mentioned before, the image centroid is an average coordinate of the pixels having count values larger than the imaging threshold. And as can be seen in formula [2], the imaging threshold can be changed depending on the threshold coefficient. In this step, the threshold coefficient can be, for example, 50%. The difference in slice No. for p-th phase will be expressed as d[p]. The step 226 indicates the step seeking this d[p]. Please note that d[1] may be defined as 0. Please note that the basis of said number difference does not need to be the 1st phase. In another word, the p in which d[p]=0 does not need to be 1 in all implementations.

In the loop defined by steps 232 and 236, summations of pixel values of phase data are performed slice by slice. Said d[p] are taken into account in this step. For example, assuming that Phase_slice [p][i] expresses a pixel value in i-th slice of p-th phase data, and Summed_slice[i] expresses a value of a pixel of the i-th slide of the summed image data located in the same position in the 2D plane as the Phase_slice[p][i], the Summed_slice[i] is calculated based on the following formula.

$$\text{Summed\_slice}[i] = \sum_{p=1}^{n} \text{Phase\_slice}[p][i + d[p]] \quad \text{[Formula 3]}$$

As can be seen in this formula, the summation in step 234 is performed after adjusting the slice positions so that the image centroids of respective phase image data can be consistent with respect to the z direction of the phase image data (direction perpendicular to short axis slices). The formula 3 expresses the calculations to be performed in step 234. Please note that the summation calculations may be performed pixel by pixel.

It should be noted that i+d[p] may be less than 0 or greater then the largest slice number, because d[p] would not generally be 0. In such cases, Phase_slice[p][i+d[p]] may be regarded as 0, for example. Or, the Summed_slice[i] may be defined as 0 in the region where i is small or large without calculating the formula [3]. It does not affect the result because the myocardium does not exist at the edge region of i in most of the cases.

In step 238, pixel values of summed image data are normalized or rounded-off. Just after the loop 232-236, some of the pixel values of pixels of the summed image data may exceed the dynamic range. So the pixel values of pixels of the summed image have to be adjusted so that the even maximum pixel value of the summed image does not exceed the dynamic range. For example, if the dynamic range of the summed image data is eight bit, it may be preferable to apply a division by Vmax/255 to the pixel value of each pixel of the summed image data, where Vmax expresses the maximum pixel value of the summed image data just after exiting from the loop 232-236.

Step 240 indicates the end of the process. At this stage, the summed image data which is subjected to the later processing has been completed. In some embodiments, the resulting summed image data may be stored in auxiliary storage 106 (see FIG. 1A) as the summed image data 140, for example.
<Step 166—Myocardial Contour Extraction for the Summed Image Data>

In this section, example processes applicable for step 166 of FIG. 1B will be explained. In this step, the myocardial contour extraction operation is applied to the summed 3D nuclear medicine imaging data (e.g., summed image data 140), and pixels corresponding to myocardial contours are determined in the summed 3D nuclear medicine imaging data. The presented examples determine following information from the summed image data 140.

myocardial contours
ventricle center slice (a short axis slice in which the cardiac ventricle exists)
ventricle center of the ventricle center slice
ventricle base beginning slice (a short axis slice from which the ventricle base region begins, from the viewpoint of the ventricle center)
ventricle center in the ventricle base beginning slice
intermediate slice (a short axis slice located at the middle of the ventricle center slice and the ventricle base beginning slice)
ventricle center in the intermediate slice Any existing technologies can be employed for extracting myocardial contours in step 166. For example, it is possible to use algorithms which the applicant disclosed in WO2013/047496 or JP patent application No. 2013-062441. Or, it is possible to use the other existing technologies mentioned in the background portion of this description for contour extraction. Just as an example, the algorithm disclosed by the applicant in JP patent application No. 2013-062441 will be explained in the present application.

Figure 3:
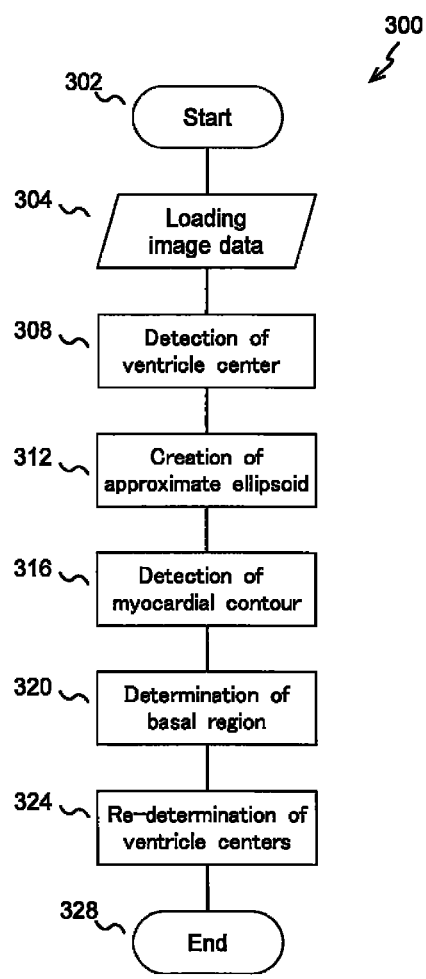
FIG. 3: a flow chart for explaining a myocardial contour extraction technique which can be applied for the summed image data in the disclosed examples.

FIG. 3 is a flow chart for explaining a basic flow of myocardial contour extraction process 300 disclosed in JP patent application No. 2013-062441. Step 302 indicates a start of the process. In step 304, the image data subjected to the myocardial contour extraction process of step 166 is loaded. This data may be the image data 140. In step 308, an operation for automatic determination of the center of the cardiac ventricle (usually left ventricle) imaged in the image data 140 is performed. In step 312, an ellipsoid is created based on the ventricle center determined in step 308. This ellipsoid will be a basis for the myocardial contour extraction process. In step 316, the myocardial contour extraction process is performed based on the created ellipsoid. In this step, myocardial contour points (inner- and outer-myocardial wall points) are determined. In step 320, an operation for determining ventricle base is performed. In step 324, ventricle centers are re-determined for respective short axis slices. Details of these steps will be explained below.
<<Step 308—Ventricle Center Detection for Summed Image>>

Figure 4:
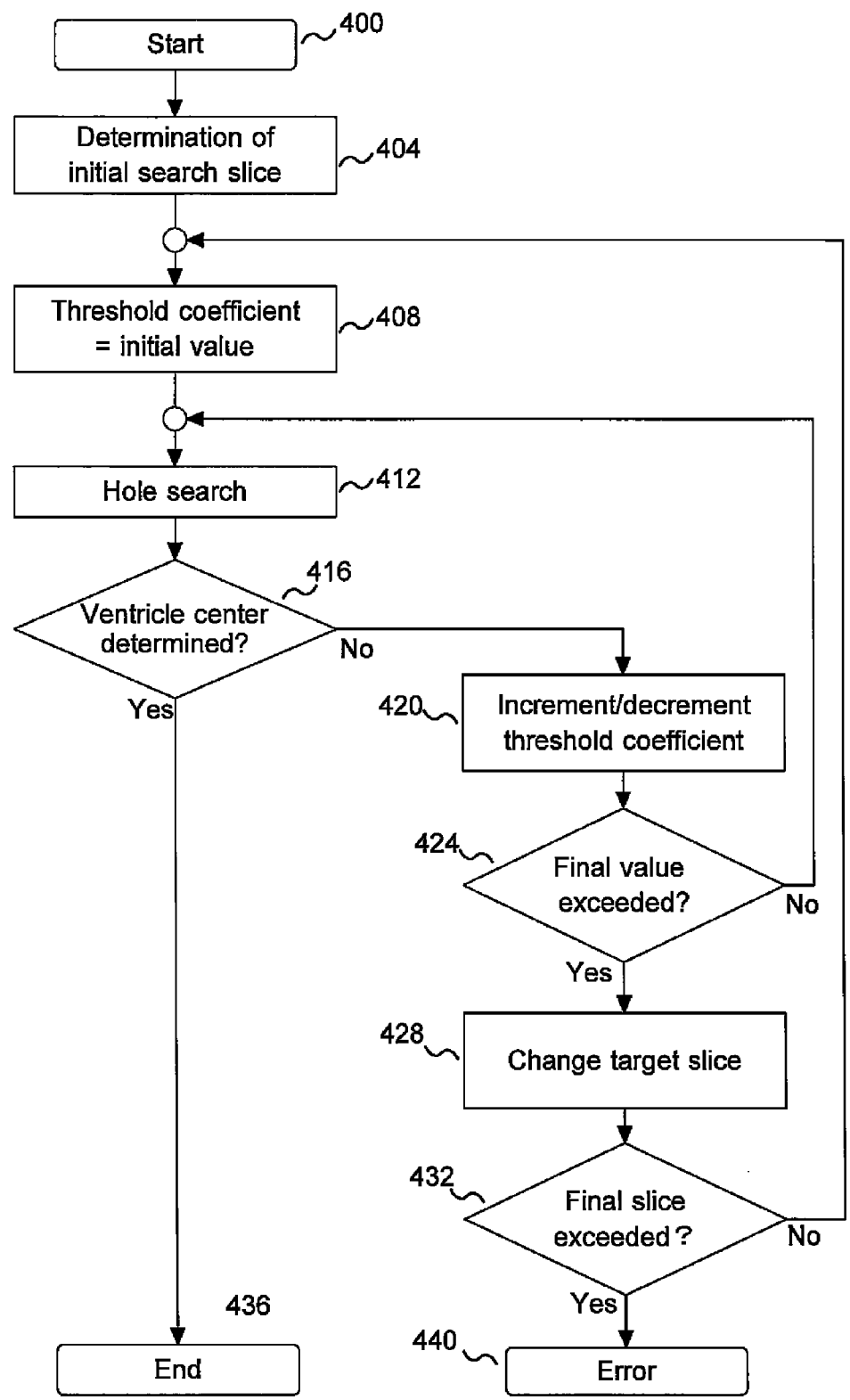
FIG. 4: a flow chart for explaining an example process applicable to step 308 of FIG. 3.

An example of ventricle center determination process of step 308 will now be explained with reference to a flow chart in FIG. 4.

Step 400 indicates a start of the process. In step 404, a slice from which a ventricle center search (initial search slice) begins is determined. The term 'slice' means the image slice including the short axis image, as in the above explanations. The image data 140 can be understood as a set of short axis image slices. The initial search slice is the slice in which the ventricle center may be located among this set of short axis images slice. For example, the initial search slice may be a short axis image slice in which the image centroid exists, where the image centroid corresponds to an average coordinate of all the pixels having pixel values greater than the imaging threshold (see formula 2). According to the study of the inventor, threshold coefficient around 50% seems to be preferable for the calculation of formula 2 for step 404 for a good result.

From step 408, the ventricle center search will be performed for the current slice that is the target of the search. The imaging threshold defined by the formula 2 is also used in this step. And in this step, the initial value of the imaging threshold is set for the current slice subjected to the ventricle center search. In other words, the initial value of the threshold coefficient (see formula 2) is set. This initial value can be set as any value by an operator. But according to the study of the inventor, it is recommended to set as around 30% for the effective search.

In step 412, a ventricle center search is performed. For example, the ventricle center search may be performed as follows.

(Substep 1) Labeling pixels having pixel values greater than the current imaging threshold (e.g., the initial threshold set in step 408) for the current slice to be searched. And determining a label which has the largest size. Please note that the "labeling" is a process generally used in the field of image processing. And it is the process for assigning the same label (for example, same number) to pixels located continuously with each other. The label having the largest size means the label having the largest number of pixels of the same label (number, for example). It does not mean that the largest value of the numeral (label). For example, suppose that numeral 1-3 are used as the labels, the number of pixels to which the label 1 is assigned is 10, the number of pixels to which the label 2 is assigned is 40, and the number of pixels to which the label 3 is assigned is 5. Then the label having the largest size is label 2.

(Substep 2) Determining a center of the area defined by the label having the largest size. Hereinafter this center may be called as 'largest label center'.

(Substep 3) Labeling pixels having pixel values smaller than the current imaging threshold in the area defined by the label having the largest size. Just for distinguishing from the label used in substep 1, the label used in substep 3 may be called as 'hole label'.

(Substep 4) Checking whether the assigned hole labels satisfy one of the following conditions. The hole labels satisfying any of those conditions will be excluded from the subsequent processing.

The center of the hole label locates near the edge of the slice.

The reason of excluding such hole labels from the subsequent processing is because the ventricle center would not locate near the edge of the slice. For example, the hole labels of which the distance between the center and the edge of the slice is less than, e.g., 40 mm, may be excluded from the subsequent processing. Please note that the center of the hole label may be an average coordinate of the hole label.

The center of the hole label locates in the septum area.

However, the location of septum area has to be estimated by some ways. One of such ways may be as follows. First, a labeling operation is performed such that pixels having pixel values greater than the initial value of the imaging threshold are labelled in the current slice for the search. Then, the septum area may be defined as the left side area of the label located at the most left side in the region located upper side from an average coordinate of the label having the largest size, assuming that the anterior wall is located at upper side of the slice. Please note that the orientation of the cardiac ventricle in the short axis image data has practically been standardized in the field of PET and SPECT; the pixels are usually arranged such that the anterior wall is displayed at upper side and the septum area is displayed at left side, when the short axis image data is displayed on a display device.

The size of the label is considered as less than 1 cm$^2$.

(Substep 5) If there is only one hole label which does not meet any of the conditions in substep 4, then the ventricle center is determined as a center of this hole label. If there are several hole labels which do not meet any of the conditions in substep 4, then the ventricle center is determined as a center of one of those hole labels that is the closest to the 'largest label center' calculated in substep 2. The data of coordinate of the determined ventricle center may be then stored to main memory 104 or auxiliary storage 106 by CPU 102 in accordance with the program 113 so that it can be used for the subsequent processing.

In step 416, it is checked that whether the ventricle center has been determined in step 412. If the ventricle center has been determined, then the ventricle center search process will be finished (step 436). If the ventricle center has not been determined, then the process moves to step 420, changes the imaging threshold, and run the ventricle center search again with the updated imaging threshold (424, 412).

The change of the imaging threshold in step 420 may be performed as follows.

(1) Initially, the imaging threshold is increased each time when the processing loop comes back to step 420. For example, threshold coefficient may be increased e.g., 5% from the initial value (which was 30% in the above example) each time when the processing loop comes back to step 420.

(2) If the ventricle center is still not determined even the threshold coefficient reaches a predetermined value (e.g., 50%), then the threshold coefficient is set as lower than its initial value (it was 30% in the above example). For example, it may be set as 28%. Then, each time when the processing loop comes back to step 420, the threshold coefficient is decreased by a predetermined value. For example, threshold coefficient may be decreased e.g., 2% each time when the processing loop comes back to step 420.

In step 424, it is checked that whether the threshold coefficient becomes lower than the search finishing value. The search finishing value can be set by an operator's own decision. For example, it can be 10%. If the threshold coefficient becomes lower than the search finishing value, then the process moves to step 428, and changes the slice to be searched for the ventricle center. For example, the next slice which locates basal side from the current slice may be selected as the new slice to be searched for the ventricle center. If the ventricle center can be determined in the current slice with the current imaging threshold (threshold coefficient), then the process is finished without searching for other slices (step 436). If the ventricle center cannot be determined even the slice reaches the final searching slice even after repeating steps 408-432, then an error output is generated (step 440). The final searching slice can be set by operator's own decision. For example, the final searching slice may be the slice which does not have any pixels having pixel values greater than the imaging threshold with a predetermined threshold coefficient (e.g., 30%).

Although some concrete values (such as 30% or 50%) are presented for the threshold coefficient in the above texts, it should be understood that they are merely examples. Some other concrete values will also be used in the present description. But all concrete values used in this description and the drawings are just examples. There are a lot of variations of the embodiments using different values.

<<Step 312—Calculation of Approximate Ellipsoid>>

Figure 5:
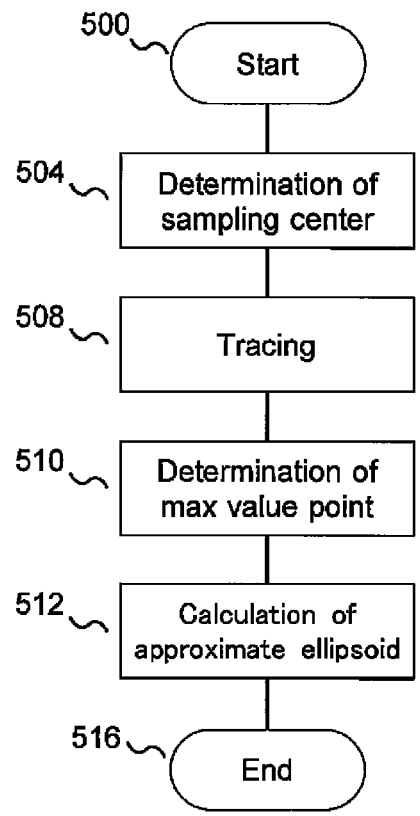
FIG. 5: a flow chart for explaining an example process applicable to step 312 of FIG. 3.

Here, an example process applicable to step 312 of FIG. 3 will be explained with reference to FIG. 5. In this step, an approximate ellipsoid is created, which will be a basis for performing myocardial contour extraction in the next step 316.

Step 500 indicates a start of the process. In step 504, a sampling center is determined, which will be a base point for sampling points to be bases for creating the approximate ellipsoid. In some embodiments, this sampling center can be created manually by an operator of system 100. In some embodiments, this sampling center can be the ventricle center decided in step 308. In some embodiments, this sampling center may be decided by following substeps.

(Substep 1) In the short axis image to which the ventricle center determined in step 308 belongs, scanning pixel values from the ventricle center radially, and determining a point (pixel) having the maximum pixel value for each scanning direction.

(Substep 2) Seeking a circle which approximates the set of points having the maximum pixel value determined in substep 1.

(Substep 3) Deciding the center of the approximate circle sought in substep 2 as the sampling center.

It is possible to seek the approximate circle in several ways. For example, the approximate circle may be defined as a circle of which the center coordinate corresponds to an average coordinate of all of the maximum pixel value points, and the radius corresponds to an average distance between the center coordinate and respective maximum pixel value points. The approximate circle may further be refined by the approach of minimizing the squire sum of residuals by changing the center coordinate and the radius.

In step 508, pixels of the image data 140 are sampled sphere-radially from the sampling center decided in step 504 to check changes of pixel values. That is, image data 140 is scanned from the sampling center to various directions three dimensionally. Then a point (pixel) having the maximum pixel value is determined for each scanning direction (step 510). Then, an ellipsoid approximating the set of determined maximum pixel value points is calculated in step 512.

In some embodiments, steps 508-512 may be performed as follows.

(Substep 1) Defining Z-axis as an axis containing the sampling center decided in step 504 and extending from ventricle base to ventricle apex, and selecting a cross-section containing Z-axis from the image data 14. Then defining sampling directions in the selected cross-section (long axis image) such that they are defined radially from the sampling center in e.g., 10° intervals, wherein 0° is defined at the apical direction and 180° is defined at the basal direction. And sampling the image data 140 for respective sampling directions. And creating a profile of pixel value (count profile) for each of the sampling direction. But a count profile may not be created for 180°, because the myocardium would not exist in the direction of 180°. In addition, determining a point (pixel) having the maximum pixel value in each count profile.

Please note that the Z-axis may be defined as an axis perpendicular to the short axis images in the image data 140 in practice. This axis may not be consistent with the actual apical direction and basal direction so much. But it is not a problem, because, the sampling center and the Z-axis used in this step are defined merely for creating an ellipsoid, and are not used for determination of inner- and outer-myocardial wall points later.

Figure 6:
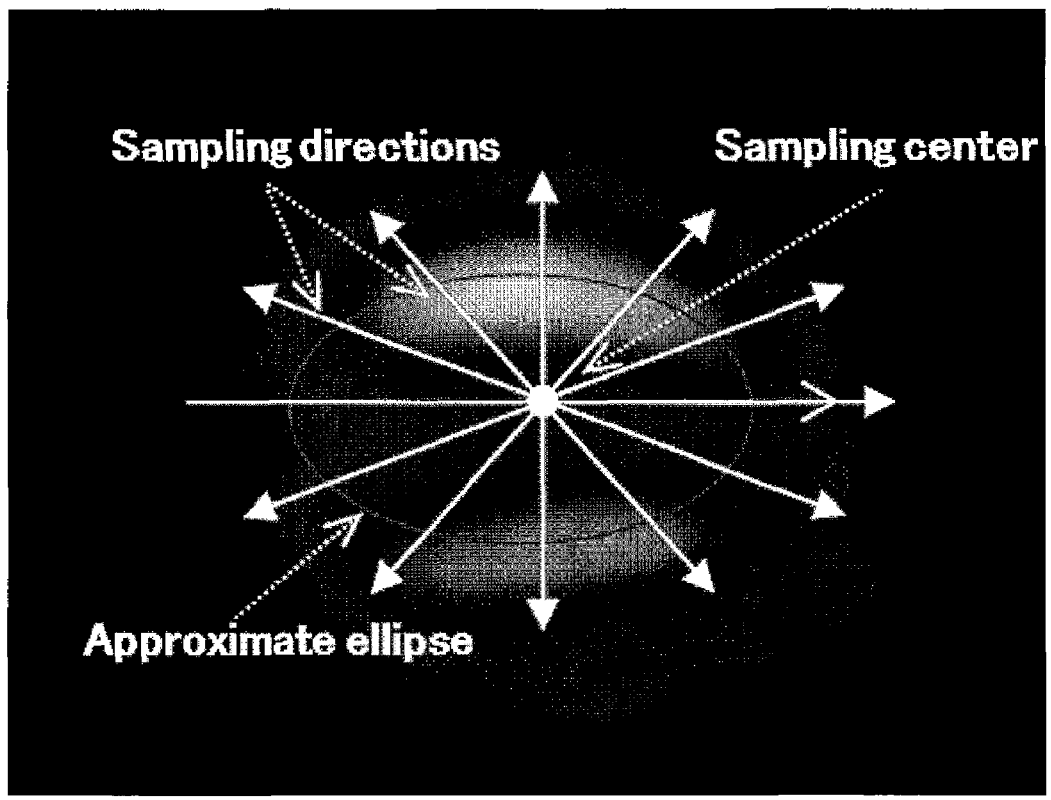
FIG. 6: an illustration for explaining an ellipsoid created in step 512 of FIG. 5.

(Substep 2) Seeking an ellipse which approximates the set of points having the maximum pixel value determined in substep 1. An example view for the sampling center, the sampling directions, and an approximate ellipse is illustrated in FIG. 6.

(Substep 3) Changing a cross-section to be used for creating count profiles, by rotating the current cross-section about Z-axis, and seeking an approximate ellipse for the new cross-section by performing the same processing as explained in substeps 1 and 2. Changing a cross-section and seeking an ellipse may be performed over 180° rotation angle about Z-axis, for example, by 10° step.

(Substep 4) Defining parameters of approximate ellipsoid such as center coordinate, main axis and minor axis based on the averages of corresponding parameters (e.g., center coordinate, main axis and minor axis) of all the approximate ellipses sought in substeps 1-3. For example, the center coordinate of the approximate ellipsoid can be the average coordinate of the center coordinates of 18 approximate ellipses sought in the last steps in case the rotation step was 10°. For example, the direction of the main axis of the approximate ellipsoid may be determined as the average direction of the main axes of the 18 approximate ellipses. The length of the main axis of the approximate ellipsoid may be determined as the average length of the main axes of the 18 approximate circles. For example, the length of the minor axis of the approximate ellipsoid may be determined as the average length of the minor axes of the 18 approximate circles. Therefore, the determined approximate ellipsoid is a spheroid, which has a circular symmetry about the main axis.

Please note that the order of the above-mentioned substeps is merely an example. For example, in some embodiments, the pixel scanning and the ellipse approximation of the maximum value points for the next cross-section may be performed after finishing these operations for the current cross-section, as in the above-presented embodiment. In some embodiments, the pixel scanning may be performed for all cross-sections in advance and then the ellipse approximations of the maximum value points may be performed for respective cross-sections.

It is possible to seek the approximate ellipse by several ways in the above-mentioned substep 2. For example, the approximate ellipse may be defined as an ellipse of which the center coordinate is an average coordinate of all of the maximum pixel value points, the length of the main axis is the longest distance from the center coordinate to the maximum pixel value points of respective count profiles, and the length of the minor axis is the shortest distance from the center coordinate to the maximum pixel value points of respective count profiles. The approximate ellipse may further be refined by the approach of minimizing the squire sum of residuals by changing the center coordinate etc.

<<Step 316—Myocardial Contour Points Detection>>

Examples of processes in step 316 of FIG. 7 are now explained with reference to FIGS. 7A-7D. In this step, pixels corresponding to inner- and outer-myocardial wall points are identified from the image data 140 based on the ellipsoid created in step 312.

Step 700 indicates a start of the process. In step 702, a cross-section containing a main axis is selected for the ellipsoid sought in step 312. This cross-section can be selected arbitrary. For example, suppose that the Z-axis is the axis containing the main axis, X-axis is perpendicular to Z-axis, and Y-axis is perpendicular to Z- and X-axes. The selected cross-section may be perpendicular to Y-axis and thus in X-Z plane. The outline of this cross-section should be an ellipse.

Figure 7A:
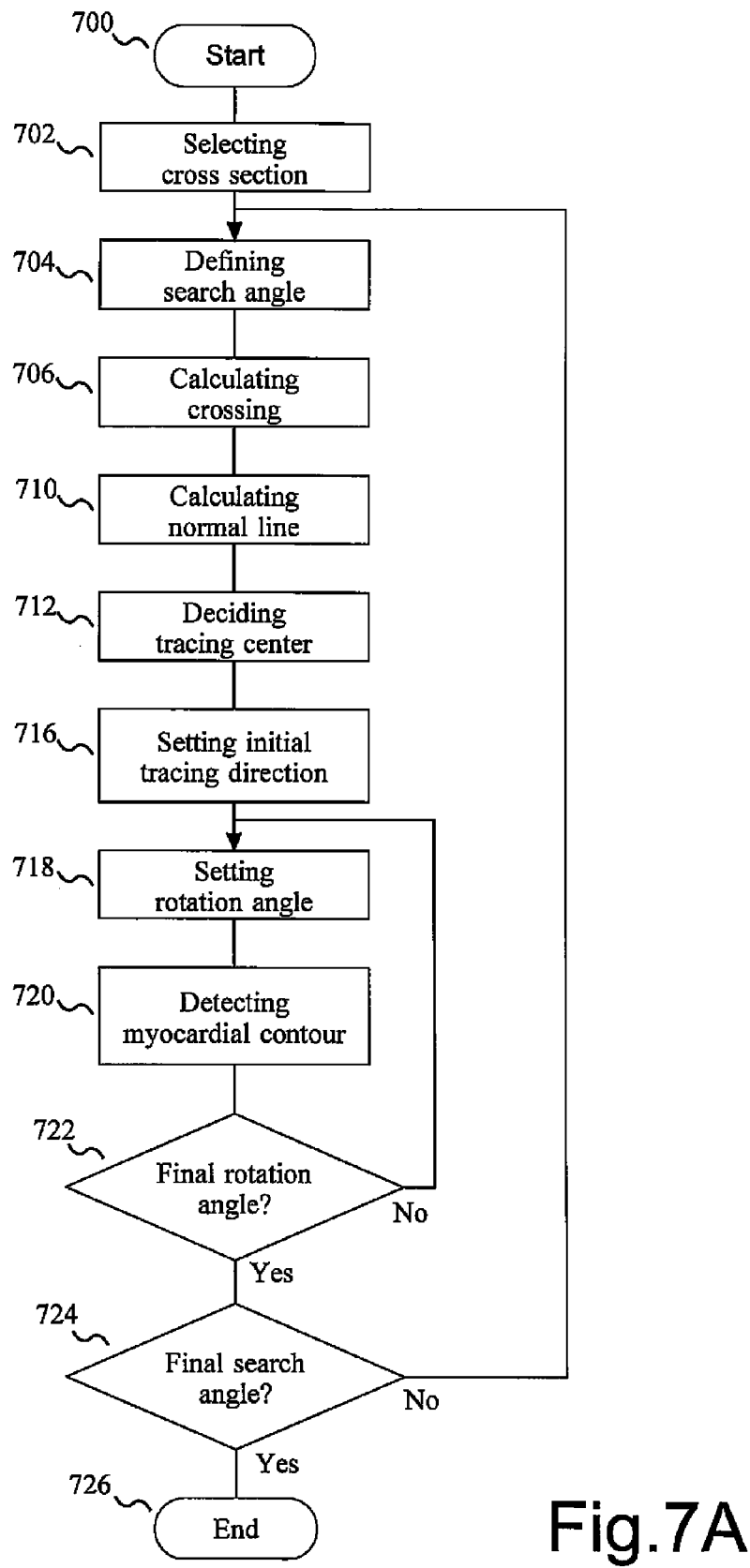
FIG. 7A: a flow chart for explaining an example process applicable to step 316 of FIG. 3.

In step 704 and subsequent steps, directions for tracing the image data 140 are defined by using the ellipse obtained in step 702, and detections myocardial contour points are conducted. In step 704, a plurality of search angles is defined, based on the definition that the origin is the center of the ellipsoid created in step 312 of FIG. 2 (=center of the ellipse obtained in step 702), 0° is defined at the apical direction on Z-axis and 180° is defined at the basal direction on Z-axis. In step 706, a crossing between the ellipse and a line extending from the ellipse center to one of the search directions is calculated for the each of the search directions defined in the last step. In this example, the initial search angle is defined as 10°. And each time when the process step comes back to step 704 from step 724, the search angle is increased by 5°. When the search angle reaches 170°, the process leaves from the loop and stops to increase the search angle. So, the 'final search angle' written in step 724 of FIG. 7A is 170°. But please note that these numeric values are just examples. It is of course possible to use different values for the initial search angle, the final search angle, and increment step.

In step 710, a normal line at the crossing sought in step 706 is calculated. That is, a line perpendicular to a tangent line at the crossing is calculated. In step 712, a crossing between the normal line sought in step 710 and Z-axis (i.e., the main axis of the ellipse selected in step 702) is calculated. This crossing will then be defined as a 'tracing center' for the myocardial contour points detection process in the current loop position in the loop from 704 to 724. In other words, this crossing will be used as a starting point for sampling image data for the myocardial contour detection.

In step 716, the initial tracing direction for the myocardial contour detection in this loop position is set. (The tracing direction may also be called as sampling direction or scanning direction in this description) It may be set as a direction from the tracing center to the crossing calculated in step 706. And a tracing direction vector is calculated in this step. The tracing direction vector is defined as a vector having the same direction with the tracing direction.

Figure 7B:
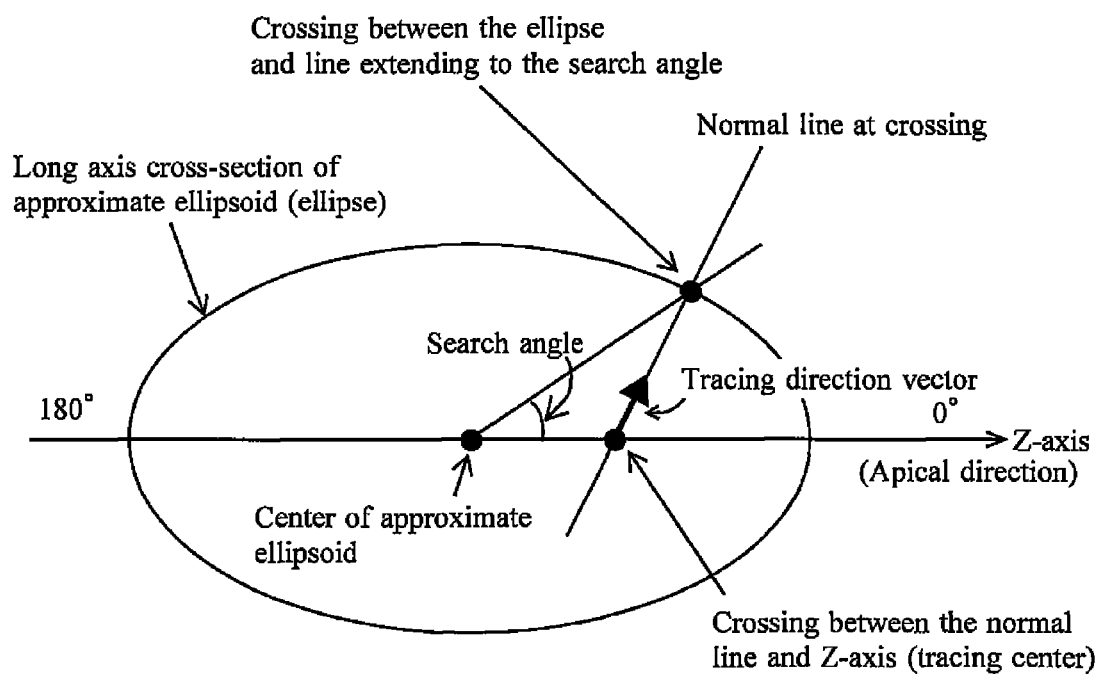
FIG. 7B: an illustration for explaining respective information related to process illustrated in FIG. 7A.

FIG. 7B illustrates an example view of the search angle, the crossing between the ellipse and a line extending to the search angle, the normal line at the crossing, the crossing between the normal line and Z-axis, and the tracing direction vector.

In step 718, a rotation angle for rotating the tracing direction vector about Z-axis (i.e., about the main axis of the ellipse) is set. In this example, the rotational angle is increased by 10° from 0° to 350° each time when the processing loop comes back to step 718 from 722. Therefore, the tracing direction vector will be rotated fully around Z-axis. And accordingly, the tracing directions will be set conical-radially with regular intervals from the point on the main axis of the ellipsoid determined in step 312, and the tracing directions are directed to the directions perpendicular to the surface of that ellipsoid. Please note that the increment step 10° used in this embodiment is of course just an example and other values such as 5° can be employed in the other embodiments. In step 720, the myocardial contour detection operation is performed in the direction of the tracing direction vector which may have been rotated in step 718. An example of the myocardial contour detection process will be presented later with reference to FIG. 7C.

In step 722, it is determined that whether the rotation angle of the tracing direction vector is the final rotation angle or not. As mentioned, the final rotation angle in this example is 350°. If the rotational angle reaches the final angle, the process moves to step 724. And it is determined that whether the current search angle set in step 704 is the final search angle or not. As mentioned, the final search angle in this example is 170°. If the search angle reaches the final search angle, the process will be finished (step 726).

Figure 7C:
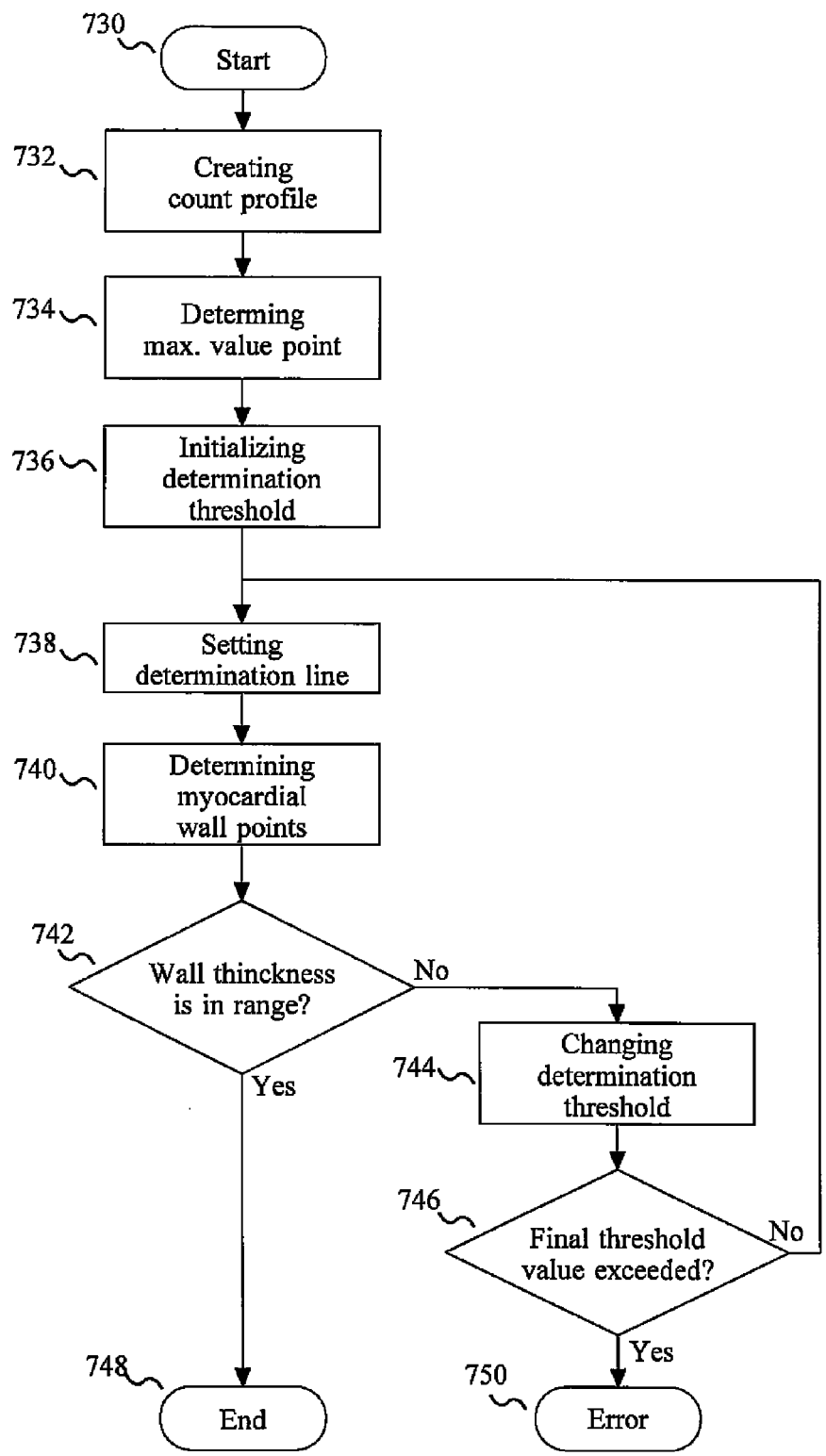
FIG. 7C: a flow chart for explaining an example process applicable to step 720 of FIG. 7A.

Next, an example of the myocardial contour detection process applicable to step 720 of FIG. 7A will be explained with reference to FIG. 7C.

Step 730 indicates a start of the process. In step 732, data scanning is performed for the image data 140 which is the subject of the myocardial contour detection in the process illustrated in step 720. The data scanning is performed from the tracing center decided in step 712 to the direction of the tracing direction vector decided in step 718. And a profile of pixel values is created as the result of scanning. In other words, changes of pixel values along the tracing direction are checked. A threshold may be used for determining an effectiveness of the pixel value in this step. For example, pixel values lower than e.g., 30% of the maximum pixel value of the current pixel value profile may be regarded as invalid or zero. Also for example, pixel having pixel values lower than the imaging threshold with the predetermined threshold coefficient (e.g., 30%) may be ignored from the further processing. It is to exclude pixels which may contain noises from the further processing.

In step 734, the point (pixel) having the maximum pixel value in the profile created in steps 732 is determined.

In step 736, a 'determination threshold' is initialized. It is a threshold used for calculating a 'determination line'. The 'determination line' is calculated in step 738. It is a reference line for determining inner- and outer-myocardial wall points in the next step 740. In some embodiment, the determination line may be decided based on the maximum value in the pixel value profile created in step 732. In some embodiments, the determination line may be decided by the following formula.

determination line=(Max value−Min value)*determination threshold+Min value.

Here, Max value is the maximum pixel value and Min value is the minimum pixel value respectively in the pixel value profile created in step 732. The determination threshold is initialized in step 736, and changed in step 744 if necessary. Re-setting of determination threshold will be explained later in connection with steps 742. Just for example, the initial determination threshold set in step 736 may be 75%. In some embodiments, the determination threshold for determining inner wall point may be different from the determination threshold for determining outer wall point.

In step 740, inner- and outer-myocardial wall points are determined as the points proximally-located to the crossings between the determination line and the line (curve) of the pixel value profile. In some embodiments, the inner myocardial wall point is determined as the crossing or its proximate among the crossings between the profile and the determination line that is located closest to the point having the maximum pixel value in the profile at the side closer to the tracing center. For example, the inner myocardial wall point is determined as the first point (pixel) in which the profile curve falls down below the determination line from the viewpoint from the maximum pixel value point to the tracing center. Similarly, in some embodiments, the outer myocardial wall point is determined as the crossing or its closest pixel among the crossings between the profile curve and the determination line that is located closest to the point having the maximum pixel value in the profile at the side opposite to the tracing center. For example, the outer myocardial wall point is determined as the first point (pixel) in which the profile curve falls down below the determination line from the viewpoint from the maximum pixel value point to the opposite of the tracing center.

Figure 7D:
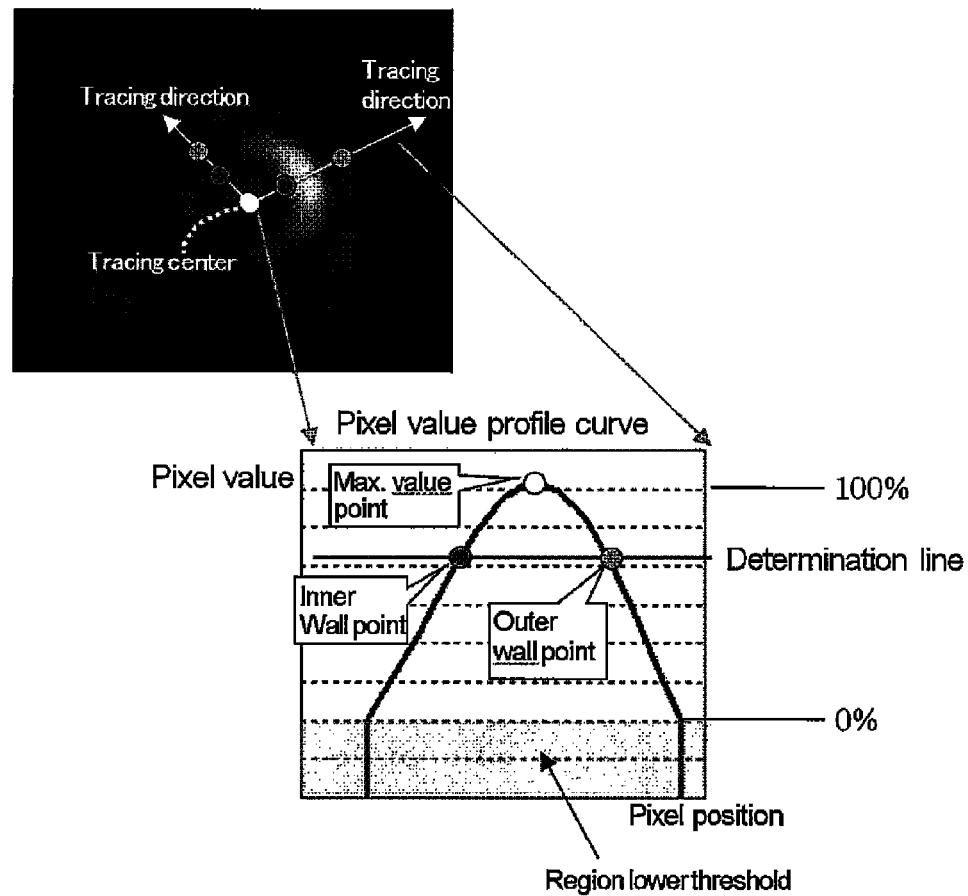
FIG. 7D: an illustration for explaining respective information related to processes illustrated in FIG. 7C.

FIG. 7D illustrates an example view for a surface for tracing the image data viewed from a position perpendicular to Z-axis, a tracing center, a tracing direction, a pixel value profile, a determination line, a point having the maximum pixel value, a point determined as an inner myocardial wall point and a point determined as an outer myocardial wall point. Please note that the shape of surface for tracing the image data is actually conical, when the search angle set in step 704 is less than 90°. So the view in FIG. 7D is a planar projection of such conical surface.

In step 742, a distance between the determined inner wall point and the outer wall point is calculated. It is also determined in this step that whether the calculated distance falls in a predetermined range or not. The distance between the inner- and outer-wall points can be considered as reflecting a thickness of myocardium. The predetermined range may be, for example, the one from 8 mm to 32 mm. This range is just an example; however, according to the study of the inventor, this range provides good results in myocardial contour detection process for both the subjects having healthy myocardium and the subjects having some problems in myocardium such as a disease causing the myocardium being thinner. If the distance between the inner- and outer-myocardial wall base points does not fall in the predetermined range, the process moves to step 744, and changes the determination threshold. The step of change of the threshold may be 5%, for example. For example, if the distance between detected the inner- and outer-myocardial wall points is less than 8 mm, the determination threshold may be decreased by 5%. And for example, if the distance between the detected inner- and outer-myocardial wall points is greater than 32 mm, the determination threshold may be increased by 5%. If the distance between the detected inner- and outer-myocardial wall points falls in the predetermined range, then those detection points are considered as a final detection points for the inner- and outer-myocardial wall in the process illustrated in FIG. 7C for the count profile created in step 732. And the detection process will be finished for this count profile. If the determination threshold exceeds final threshold values and the distance between the detected inner- and outer-myocardial points still does not fall in the predetermined range (step 746), the process outputs an error (step 750). And it is recorded that the inner- and outer-myocardial wall points could not be determined in the current count profile. In some embodiments, even though the process finishes as an error (step 750), some information of the inner- and outer-myocardial points may be included in an output. For example, the points detected by the initial determination line may be included in the output.

Please note that it may not be possible to determine an inner myocardial wall point in the apical region, because the surface for tracing for the contour detection (i.e., the conical surface defined in steps 704-722) may be set inside of or very close to the myocardium. Therefore, the inner wall points may not be necessary to be determined in the apical region. Only outer wall points may be determined in such region. If only the outer wall point is determined, it is not necessary to change the determination line. So the outer wall point may be determined based on the determination line corresponding to the initial determination threshold. And the determined point with the initial threshold can be considered as the final detection point as the outer myocardial wall point in the corresponding profile.

The determination whether the scanning region corresponds to the ventricle apex or not may be made based on the search angle which is set in step 704. For example, if the search angle is equal or less than 15°, it may be possible to regard that the scanning region is the apical region.

The apical end of the ventricle apex may be determined based on some or all of the outer myocardial wall points detected after finishing the process illustrated in FIG. 7A. It may be determined by approximating those outer myocardial wall points by an ellipsoid, and regarding the apical end of the ellipsoid is the apical end of the ventricle apex.

The thickness of the myocardium in the ventricle apex may be considered as the same thickness as the thickness of the other region of the myocardium. For example, the thickness of the ventricle apex may be determined based on the data of short axis slice having a center of the ellipsoid sought in step 312 and short axis slices neighboring that slice (e.g., 10 slices for the apical direction and 10 slice for the basal direction). For example, inner- and outer-myocardial wall points as well as a thickness of the myocardium may be determined in each of these short axis slices. And the average thickness of those determined thicknesses may be regarded as a thickness of the ventricle apex.

<<Step 320—Determination of Basal Region>>

Figure 8:
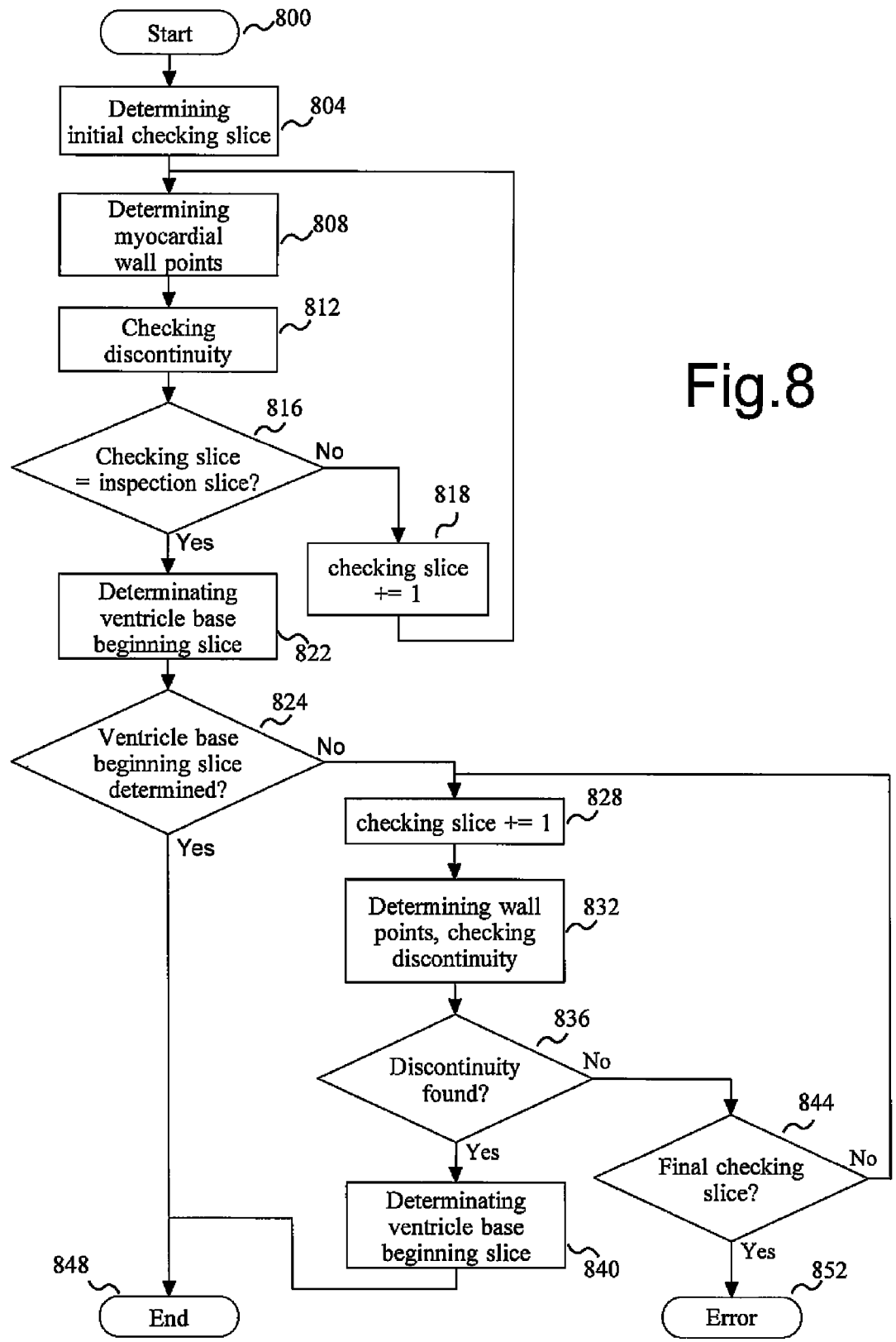
FIG. 8: a flow chart for explaining an example process applicable to step 320 of FIG. 3.

Here, example processes for determining a ventricle base region in step 320 of FIG. 3 will be explained with reference to FIG. 8. More concretely, a border of the basal region near the ventricle center is determined in this step. The determination is performed based on a checking whether there is a discontinuity of myocardial wall having a larger angle than a predetermined angle at the septal side. This checking is performed in short axis slices located in a certain area of the basal side.

Step 800 indicates a start of the process. In step 804, the initial short axis slice for checking the discontinuity will be determined in the image data 140. This slice may be determined by using the ellipsoid calculated in step 312 of FIG. 2. This ellipsoid may be called as the first ellipsoid in the following explanations. The initial slice for checking discontinuity may be determined as a slice perpendicular to the main axis of the first ellipsoid, and a slice located at 110° with respect to Z-axis, where Z-axis corresponds to the direction of the main axis of the first ellipsoid, the original point is the center of the first ellipsoid and 0° is the direction to the apical side.

In step 808, inner- and outer-myocardial wall points are determined for the slice to be checked. The determinations of the wall points may be performed by, defining a tracing center as a crossing between the main axis of the first ellipsoid and the slice to be checked, defining tracing directions radially from the tracing center in the slice to be checked, and using the method explained above in connection with FIG. 7C for the each tracing direction.

Figure 8A:
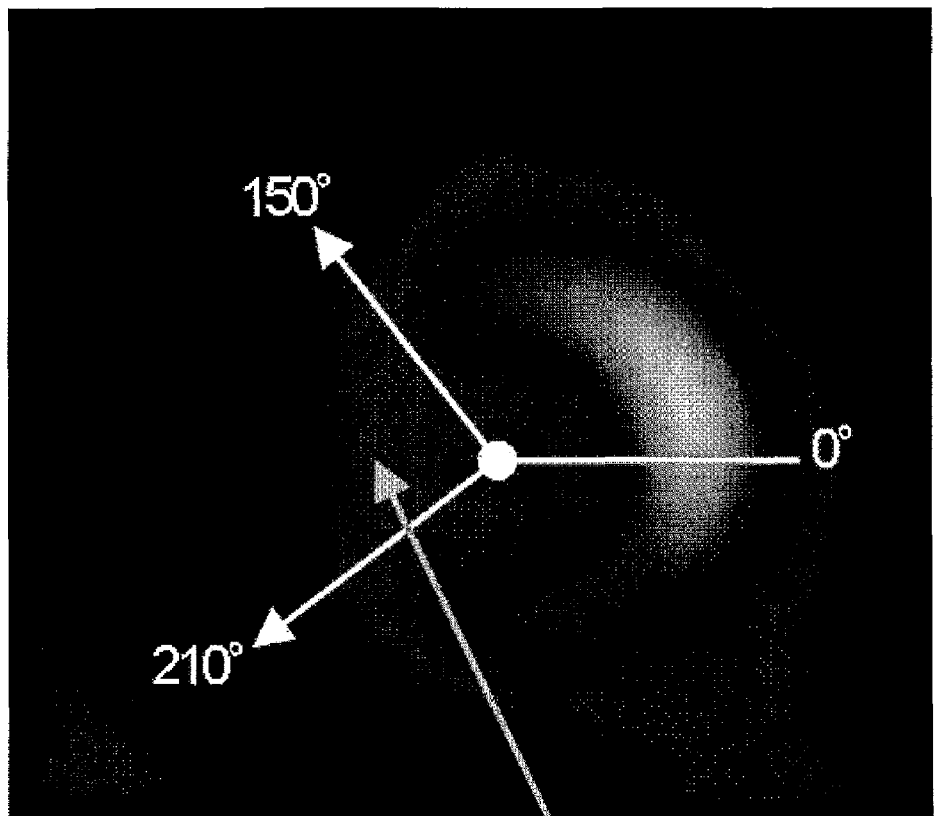
FIG. 8A: an illustration for explaining the process in step 812 of FIG. 8.

In step 812, it is checked that whether there is a discontinuity of myocardial wall having a larger angle than a predetermined angle at the septal side in the slice to be checked based on the result of step 808. The discontinuity of myocardial wall may be determined if a pixel value profile does not have a valid inner wall point and/or outer wall point. If a valid inner- and/or outer-wall point could not be determined for a pixel value profile, it can be considered there is a discontinuity in the myocardial wall in the region of angle corresponding to that profile. Please note that generally the septum locates at the left side of the short axis image if the image is obtained by the nuclear medicine imaging technology. Therefore, in a 2D polar coordinates system provided on the slice to be checked where the original point is the tracing center and 0° is defined to the horizontal and right direction when the slice is to be displayed, the septal region may be considered as, e.g., the region of 150°-210°. Please note that these angles are just examples and other values can be employed. This example of region of angle to be checked for discontinuity in myocardial wall is illustrated in FIG. 8A for reference. In step 812, it is checked that whether there is a continuous discontinuity in myocardial wall greater than a predetermined extent in angle (for example, 20°) in the region of angle to be checked.

The processing of steps 808 and 812 is performed for slice by slice from the initial short axis slice for checking determined in step 804 to a slice so called 'inspection slice'. It is illustrated in FIG. 8 by the loop shown by steps 816 and 818. The 'inspection slice' is a short axis slice located basal side with respect to said initial short axis slice for checking. The details of the inspection slice will be explained later. So the existence of discontinuity in the septal region greater than the predetermined extent of angle will be checked for each of slices from the initial slice to the inspection slice.

In step 822, the process tries to determine a short axis slice corresponding to the boarder of the ventricle base. Such slice will be called as 'ventricle base beginning slice' in this Description. It may be performed as follows.

(a) It is checked that whether the inspection slice and its sequentially neighboring slices contain discontinuities in the septal region greater than the predetermined extent of angle. If so, the 'ventricle base beginning slice' is determined as the slice located closest to the ventricle apex among those neighboring slices containing the discontinuities. For example, suppose that the result of steps 804-818 can be summarized as the following table. That is, suppose that the number (identifier) of slice and the result of the discontinuity detection can be summarized as the following table. Then the 'ventricle base beginning slice' will be determined as slice No. 54.

| Slice No. | Discontinuity | |
|---|---|---|
| 50 | No | Initial slice to be checked |
| 51 | Yes | |
| 52 | No | |
| 53 | No | |
| 54 | Yes | |
| 55 | Yes | |
| 56 | Yes | Inspection slice |

(b) If a set of sequentially adjacent slices having said discontinuity cannot be identified at the position of the inspection slice, then the search of the 'ventricle base beginning slice' will be proceeded as follows.

It is checked that whether there are slices having said discontinuity or not at the position of the inspection slice and its apical side. If such slices can be identified, then the 'ventricle base beginning slice' is determined as the slice located closest to the ventricle base among such slices.

If there is no slice having said discontinuity at the position of the inspection slice and its apical side, then the process does not determine the 'ventricle base beginning slice' in step 822. And the process moves to the next step.

In step 824, it is checked that whether the 'ventricle base beginning slice' has been determined by the steps up to here. If it is determined, then the process moves to step 848 and will be finished. If it is not determined, then the process moves to step 828.

In step 828 and subsequent steps, the slice to be checked will be changed one by one to the basal direction, and the existence of said discontinuity will be checked for the each slice by the same way as explained in connection with steps 808 and 812. In step 836, it is determined whether said discontinuity is detected in the current slice. If it is detected, then the 'ventricle base beginning slice' is determined as the current slice (step 840). If said discontinuity is not detected, the slice to be checked will be changed to the next slice, and the trial to find said discontinuity will be performed on the new slice (step 844) If the slice to be checked reaches the final slice but the discontinuity has not been found yet, then the process outputs an error and is terminated.

In the above-mentioned example process, the 'inspection slice' may be the slice located at the 135° with respect to Z-axis, where Z-axis corresponds to the direction of the main axis of the first ellipsoid, the original point is the center of the first ellipsoid and 0° is the direction to the apical side. And the 'final slice' to be checked may be the slice located at the 150° with respect to Z-axis in the same coordinate system. These angles are of course merely examples. Different embodiments can employ different angles.

Figure 8B:
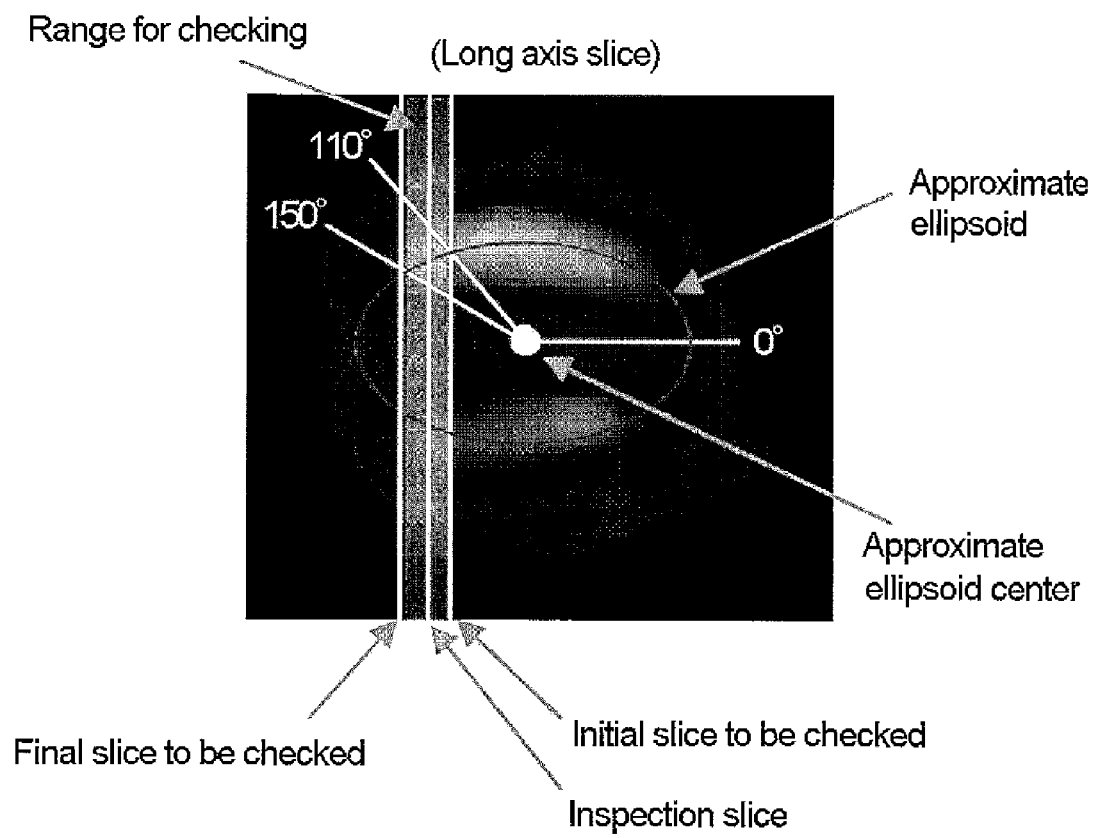
FIG. 8B: an illustration for explaining respective information related to processes illustrated in FIG. 8.

FIG. 8B illustrates an example view of the initial slice to be checked, the inspection slice, the range for determining the ventricle base beginning slice, and the final slice to be checked.

<<Step 324—Redetermination of Ventricle Center for Each Slice>>

In this subsection, an example process for re-determining ventricle centers for each slice indicated in step 324 of FIG. 3 will be explained. The term 'slice' means the image slice including the short axis image, as in the above explanations.

In one example, the ventricle center in a each slice may be re-defined as the crossing point between that slice and the main axis of the approximate ellipsoid determined in step 312. In the other example, the ventricle centers of slices located between the slice containing the center of the approximate ellipsoid and the slice located right before the ventricle base beginning slice (determined in step 320) may be re-defined by following steps.

1) defining a tracing center as a crossing point between a slice and the main axis of the approximate ellipsoid;

2) detecting myocardial contours in that slice;

3) approximating the detected myocardial outer wall points by a circle; and 4) defining the center of the approximate circle as the ventricle center of that slice.

The inventors have found that such redetermination of ventricle centers provide better results in subsequent steps. Please note that both options for re-determining ventricle centers are included in the scope of the present invention.

The ventricle centers of the ventricle base beginning slice and the slices located basal side of the ventricle base beginning slice may be re-defined as the point having the same two-dimensional coordinate point as the ventricle center of the slice located right before the ventricle base beginning slice. So the ventricle centers of these slices are located at the same position in the two-dimensional plane.

When the step 324 is finished, the processes regarding step 300 will also be finished (step 328).

<<Other Processes which May be Performed in Step 166>>

Now the essence of the myocardial contour detection algorithm disclosed in JP patent application No. 2013-062441 has been explained. However, JP patent application No. 2013-062441 and WO2013/047496 further disclose various processes for improving the quality of the myocardial contour detection, such as for corrections, interpolations and/or reshaping. It is preferable to refer to these documents. It is possible to practice the claimed embodiments without knowing the contents of JP patent application No. 2013-062441 and WO2013/047496, however, it is highly recommended to read these documents. The contents of JP patent application No. 2013-062441 and WO2013/047496 should be considered as a part of the present disclosure.

<Step 168—Determination of Myocardial Characteristic Points in the Summed Image Data>

In this section, an example process applicable to step 168 of FIG. 1B will be explained. In step 168 of FIG. 1B, a plurality of tracing directions is defined based on the summed 3D nuclear medicine imaging data. Then a reference myocardial center base point, a reference inner myocardial wall base point and a reference outer myocardial wall base point are determined for each of the tracing directions. These operations may be performed as the process 900 illustrated in the flow chart of FIG. 9.

Step 904 indicates a start of the process. In step 908, a binary image data is created by assigning a first value (for example, 1) to pixels in the image data 140 which are determined as being associated with myocardial regions, and assigning a second value (for example, 0) to pixels in the image data 140 which are determined as not being associated with myocardial regions. The determination whether respective pixels in the image data 140 are the ones for myocardial regions or not can be based on the result of the processing in the step 166.

In step 912, myocardial center base points, inner myocardial wall base points and outer myocardial wall base points are determined for the apical side based on checking changes of the pixel values at the apical side of the binary image created in the last step. In this example, this step has following substeps.

1) defining a starting point for tracing; it can be a ventricle center (slice center) of the short axis slice to which the ventricle center of the whole of the cardiac ventricle belongs (such slice has been called as the 'ventricle center slice' in the above descriptions).

2) setting tracing directions for checking changes of pixel values; such tracing directions can be set radially and three-dimensionally from the starting point at apical side.

3) determining the myocardial center base point, inner myocardial wall base point and outer myocardial wall base point for each of the tracing direction. In one variation, the ventricle center slice may be defined as the short axis slice which includes the center of the approximate ellipsoid created in step 312. In this case, the ventricle center of this slice can of course be the center of the approximate ellipsoid. In the other variation, the ventricle center slice may be defined as the short axis slice which includes the ventricle center determined in step 308 (step 416). In this case, the ventricle center of this slice can of course be the ventricle center for the above-mentioned substep 1).

As mentioned, the tracing directions may be defined radially and three-dimensionally from the starting point to the apical directions. An example of setting tracing directions is shown in FIGS. 10(a) and 10(b). In this example, four initial tracing directions are set in 20° steps with respect to Z-axis, where Z-axis is defined as an axis perpendicular to short axis slices and including the ventricle center, and 0° is defined as the direction of the ventricle apex. Then, these initial tracing directions are rotated about Z-axis respectively. In this example, they are rotated 360° in 45° steps. Based on these steps, this example sets 32 (=4 times 8) tracing directions from the ventricle center to the apical side.

FIG. 10(a) shows tracing directions on a plane including Z-axis by using one of the horizontal long axis images in the binary image created from the image data 140 in step 908. It is shown that eight tracing directions 1006 are set from the tracing center 1004 (the ventricle center in the ventricle center slice) to the myocardial region 1002 at apical side. It should be noted that the reason why eight tracing directions 1006 are shown and not four is that rotating a tracing direction 180° about Z-axis results in setting a tracing direction in the same plane as the original tracing direction is set.

FIG. 10(b) shows eight tracing directions defined by rotating one of the four initial tracing directions about Z-axis. For better understanding, FIG. 10(b) shows these tracing directions by projecting them on a short axis image in the binary image created from the image data 140 at step 908. It is illustrated that tracing directions 1006 are defined radially in 45° steps from the ventricle center 1004.

Figure 11:
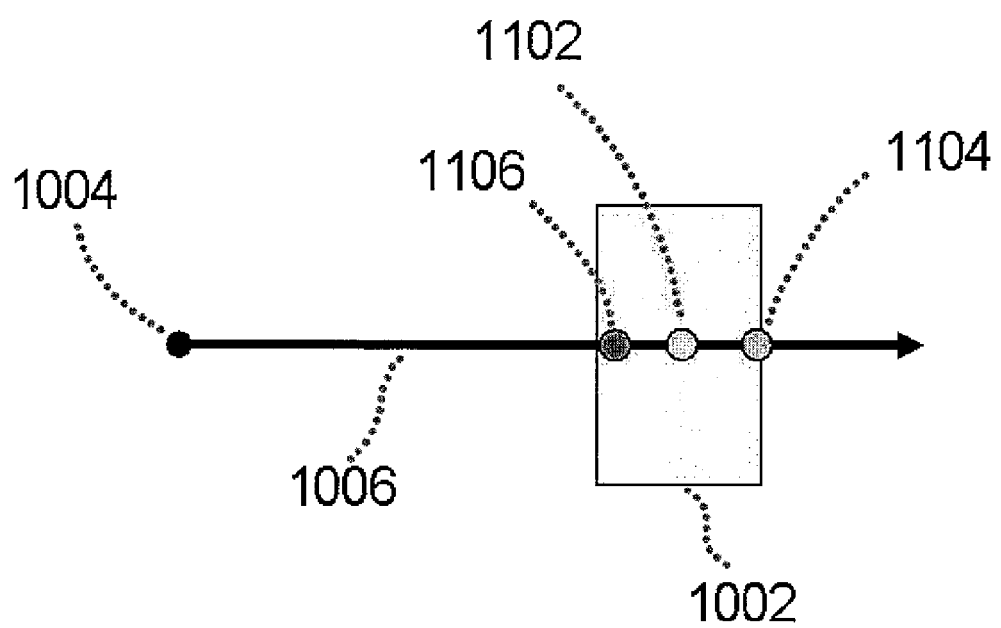
FIG. 11: an illustration for explaining examples of reference myocardial center base points, reference inner myocardial wall base points, and reference outer myocardial wall base points which may be determined in step 912 of FIG. 9.

The myocardial center base point, the inner myocardial wall base point and the outer myocardial wall base point for each tracing direction may be determined as illustrated in FIG. 11, for example. Firstly, detecting the inner edge point and the outer edge point of the myocardial region 1002 along the tracing direction 1006 by checking changes of pixel values of the binary image created in step 908 along the tracing direction 1006 from the tracing starting point 1004. Since the pixel values have been binarized, this detection is an easy operation. The myocardial center base point 1102 is decided as the middle point between the inner edge point and the outer edge point. And the outer myocardial wall base point 1104 is decided as the outer edge point, i.e., the edge point which locates farther than the other edge point from the starting point 1004. The inner myocardial wall base point can be decided as the inner edge point. However, the inventors have found that it is better to define the inner myocardial wall base point at a point slightly inside of the myocardial region for obtaining a better final result. Therefore, the inner myocardial wall base point 1106 in this example is decided as the point located at a certain distance from the middle point of the edge points at inner side along the tracing direction 1006, where the certain distance may be 90% of the distance between said middle point and the inner edge point. In step 912, myocardial center base points, inner myocardial wall base points and outer myocardial wall base points are decided for all the tracing directions which have been set earlier in this step.

In step 916, myocardial center base points, inner myocardial wall base points and outer myocardial wall base points are determined for the central area of the myocardium. In this step, tracing directions are defined at the central area of the myocardium in the binary image created in step 908, then changes of the pixel values are checked in respective tracing directions. And then myocardial center base points, inner myocardial wall base points and outer myocardial wall base points are determined for respective tracing directions as in step 912.

The tracing directions defined in step 916 may be set as radially and two-dimensionally in the short axis slice (i.e., in the short axis plane). The short axis slices to which the tracing directions are defined may be the ventricle center slice (the short axis slice includes the center of the approximate ellipsoid created in step 312), the ventricle base beginning slice (which has been determined in step 822), and a short axis slice located at the middle of these two slices. So the tracing directions may be defined in three slices, in some embodiments.

FIG. 10(c) shows an example view of the tracing directions set in step 916. As similar to FIG. 10(a), the view of FIG. 10(c) is also created by using a horizontal long axis image. As can been seen in this view, the tracing directions are defined perpendicular to Z-axis and from ventricle center 1004 of the ventricle center slice, ventricle center 1008 of the ventricle base beginning slice, and ventricle center 1010 of the slice located at the middle of said two slices respectively. In each short axis slice, the tracing directions may be defined in 45° steps from the starting point that may correspond to the ventricle center in that slice. Accordingly, 24 tracing directions (8 tracing directions for each of the 3 slices) are defined in this example. Then, change of the pixel values are checked, and a myocardial center base point, an inner myocardial wall base point and an outer myocardial wall base point are determined for each of the tracing directions by the way which has been explained above by referring to FIG. 11.

In step 920, myocardial center base points, inner myocardial wall base points and outer myocardial wall base points are determined for the basal area of the myocardium. In this step, tracing directions are defined at the basal area of the myocardium in the binary image created in step 908, then changes of the pixel values are checked in respective tracing directions for determining respective detection points.

The tracing directions defined in step 920 may be set as radially and three-dimensionally from a predetermined starting point in the ventricle to the basal side. This predetermined starting point may be the ventricle center determined in step 324 for the ventricle base beginning slice determined in step 822. The tracing directions may be set by: defining several initial tracing directions with respect to Z-axis, for example, three initial tracing directions with 20° steps from the starting point, where 0° is defined as the direction to the ventricle base; and setting final tracing directions by rotating the initial tracing directions about Z-axis in, for example, 45° steps.

FIG. 10(d) shows an example view of the tracing directions set in step 920. As similar to FIG. 10(a), the view of FIG. 10(d) is also created by using a horizontal long axis image. It is shown that tracing directions 1012 are set radially from the ventricle center 1008 of the ventricle base beginning slice. Then, a myocardial center base point, an inner myocardial wall base point and an outer myocardial wall base point are determined for each of the tracing directions defined in the above steps by the way that has been explained before with reference to FIG. 11.

FIG. 10(e) illustrates all the exemplary tracing directions defined in the above-mentioned steps for the apical region, the center region, and the basal region of the ventricle by overlapping to a horizontal long axis image.

Figure 12:
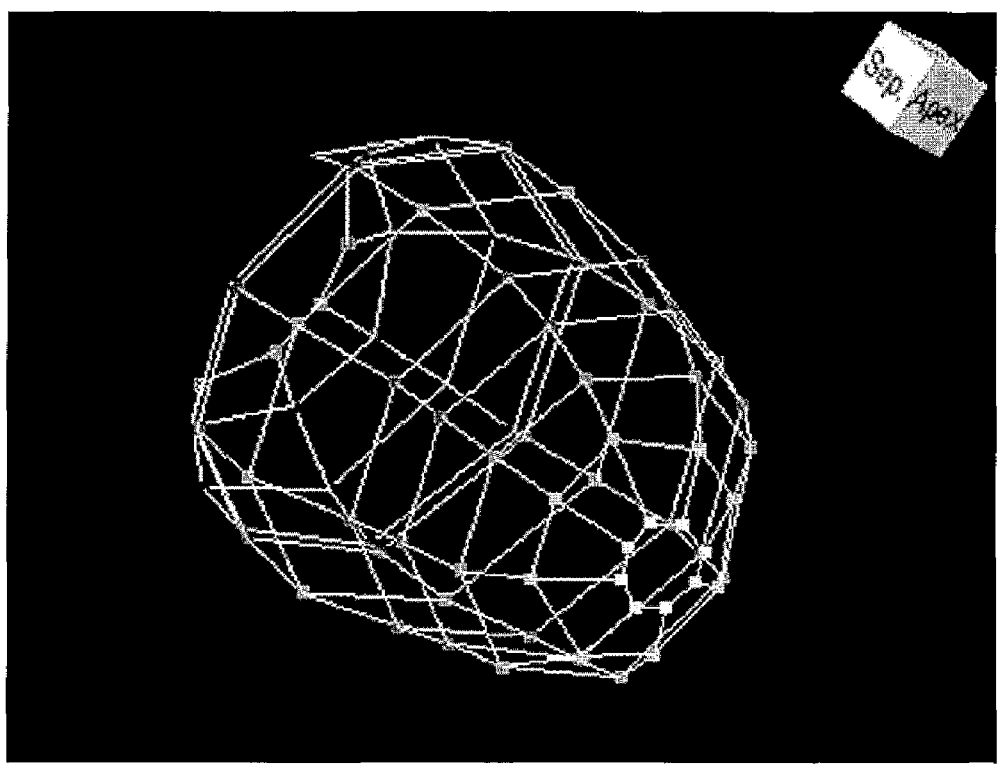
FIG. 12: an illustration for presenting a view of the reference myocardial center base points determined in step 900 of FIG. 9 as an example.

When the steps 912-920 are completed, myocardial center base points, inner myocardial wall base points and outer myocardial wall base points should have been determined for all over the myocardial regions. Then the process 900 will be finished (924). In this specification, the myocardial center base points, the inner myocardial wall base points and the outer myocardial wall base points determined for the summed image data may be called as the reference myocardial center base points, the reference inner myocardial wall base points and the reference outer myocardial wall base points respectively. Just for an example, FIG. 12 shows the reference myocardial center base points determined in above example. Those points are connected by line, just for illustration purpose.

<Step 170—Determinations of Myocardial Center Points for Each of the Phase Images>

Figure 13:
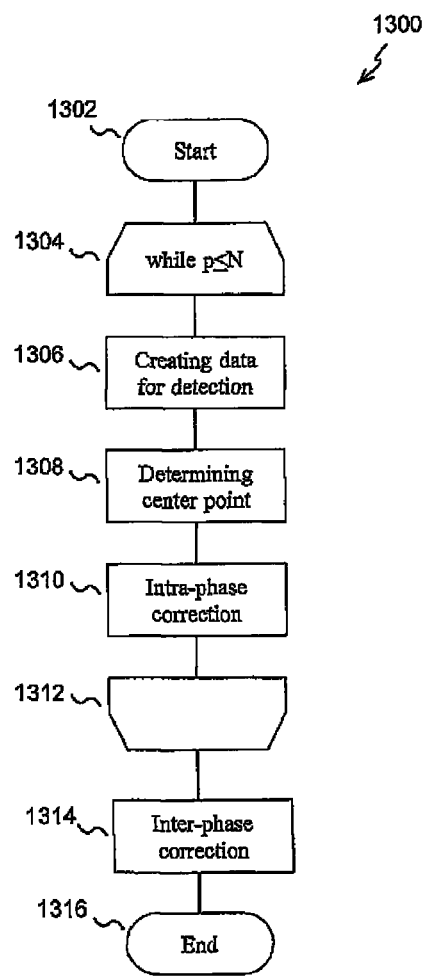
FIG. 13: a flow chart for explaining an example process applicable to step 170 of FIG. 1.

In this section, an example process applicable to step 170 of FIG. 1B will be explained with reference to FIG. 13. The example process 1300 that is applicable to step 170 of FIG. 1B determines myocardial center base points for each cardiac phase based on the corresponding 3D SPECT data (for example, image data 131-138).

Step 1302 indicates a beginning of the process. The loop defined by 1304-1312 indicates that the myocardial center base points are determined for each of the cardiac phase related with the myocardial contour detection of the examples explained in this description. With this regard, the p in step 1804 is changed from 1 to 8, since this example involves eight phases corresponding to image data 131-138.

In step 1306, an image data for detecting the myocardial center base points is created. In one simple example, this image data can be identical with one of the image data 131-138 corresponding to the current loop position. However, in this example, the image data created in step 1306 for the purpose of point detection is created by incorporating neighboring phase image data to the image data corresponding to the current loop position. Such step is useful for smoothing position changes of the detected myocardial center base points between the phases. In one example, the image data created in this step for myocardial point detection may be created by adding the pixel values of the corresponding pixels of the neighboring phase image data to the pixels of the image data corresponding to the current loop position. If the loop position is the first or the last position, only existing one of the previous and next neighboring phase image data may be added. If the loop position is in the other position, both the previous and next neighboring phase image data may be added.

In step 1308, the myocardial center base points are determined for the image data created in step 1306. The myocardial center base points determined in this step may be called as the phase-specific myocardial center base points in this specification. The tracing directions for determining the base points may be the same as the ones defined for the summed image data 140, i.e., same as the ones defined for the binary image data created in the process 900 of FIG. 9. That is, these tracing directions can be the same as the ones defined in steps 912-920 of FIG. 9.

In each tracing direction, the phase-specific myocardial center base point may be the point (pixel) having the maximum pixel value on that tracing direction.

Figure 9:
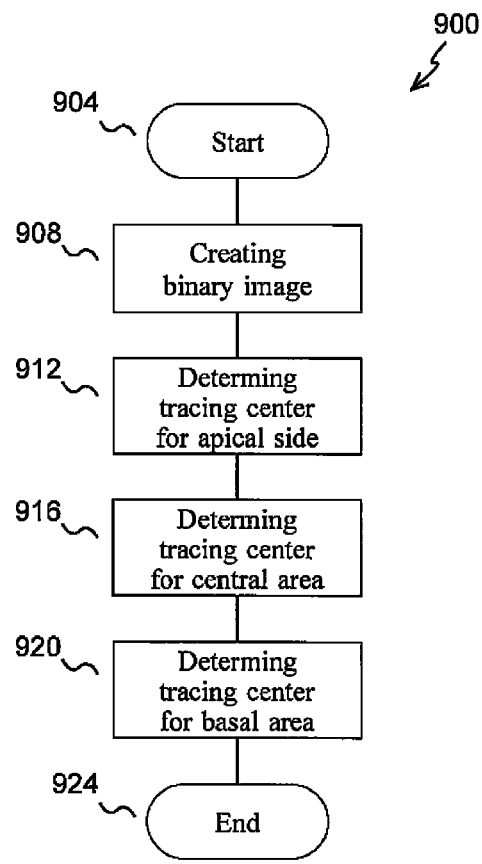
FIG. 9: a flow chart for explaining an example process applicable to step 168 of FIG. 1.

In some embodiments, the range for checking variations of the pixel values in each tracing direction may be limited to the range close to the reference myocardial center base point (i.e., the myocardial center base point determined in the process 900 of FIG. 9) in that tracing direction. For example, the range may be defined as ±20 mm of the myocardial center base point determined for the summed image data 140 on that tracing direction. In some embodiments, the far side of the reference outer myocardial wall base point with respect to the tracing center may be excluded from the range for detecting a phase-specific myocardial center base point. In some embodiments, the area for detecting a phase-specific myocardial center base point may not be limited on the tracing direction. It may be expanded to the area neighboring to the tracing direction. For example, the area comprising +2 pixels and −2 pixels along Z-axis (e.g., long axis of the ventricle) with respect to the tracing direction may be included for detecting the pixel having the maximum pixel value. In another example, the cylindrical area of which the central axis corresponds to the tracing direction and the radius corresponds to e.g., 3 pixels may be regarded as the area for detecting the phase-specific myocardial center base point.

In the other example, the phase-specific myocardial center base point may be determined not only by a pixel value of a single pixel but also by pixel values of a plurality of pixels. For example, the phase-specific myocardial center base point may be determined as the point corresponding to the pixel in which the summed value of its own pixel value and pixel values of the neighboring pixels (e.g., ±2 pixels) becomes maximum. If the number of pixels in the area for detection is small, the base point may be determined as the point corresponding to the pixel in which the summed pixel values of its own and neighboring ±1 pixels becomes maximum.

In step 1310, smoothing operations are applied for the phase-specific myocardial center base point determined in step 1308. The position correction operations explained in this step are not essential operations for all of the embodiments of the present invention. However, the smoothing operation provides an advantage that the extracted myocardial contours become smoother. In this example, following two smoothing operations are applied.

[1] Smoothing Along Z-Axis

As explained above with reference to FIG. 10(b), the tracing directions in the above example were defined by rotating initial tracing directions (having some angles with respect to Z-axis respectively) about Z-axis. Therefore, some tracing directions have the same rotation angle about Z-axis. That is, some tracing directions have the same angle if they are projected on a plane perpendicular to Z-axis. The phase-specific myocardial center base points have been determined for these tracing directions. Hence, the inventors has considered to apply a smoothing operation for each set of phase-specific myocardial center base points having the same rotation angle about Z-axis.

It should be noted that Z-axis used in steps 912, 916 and 920 are different, as can be seen in FIG. 10(e), as the tracing centers (original points) are different. (Z-axis in those steps were defined as an axis perpendicular to the short axis slice and passes the tracing center.) However, since these Z-axes are all parallel, the smoothing operation explained here ignores the differences of the original points and considers only the rotation angles about Z-axes. Hence the smoothing operation in this step is applied for a set of phase-specific myocardial center base points having the same rotation angle about Z-axis regardless of the differences of the tracing center.

Figure 14A:
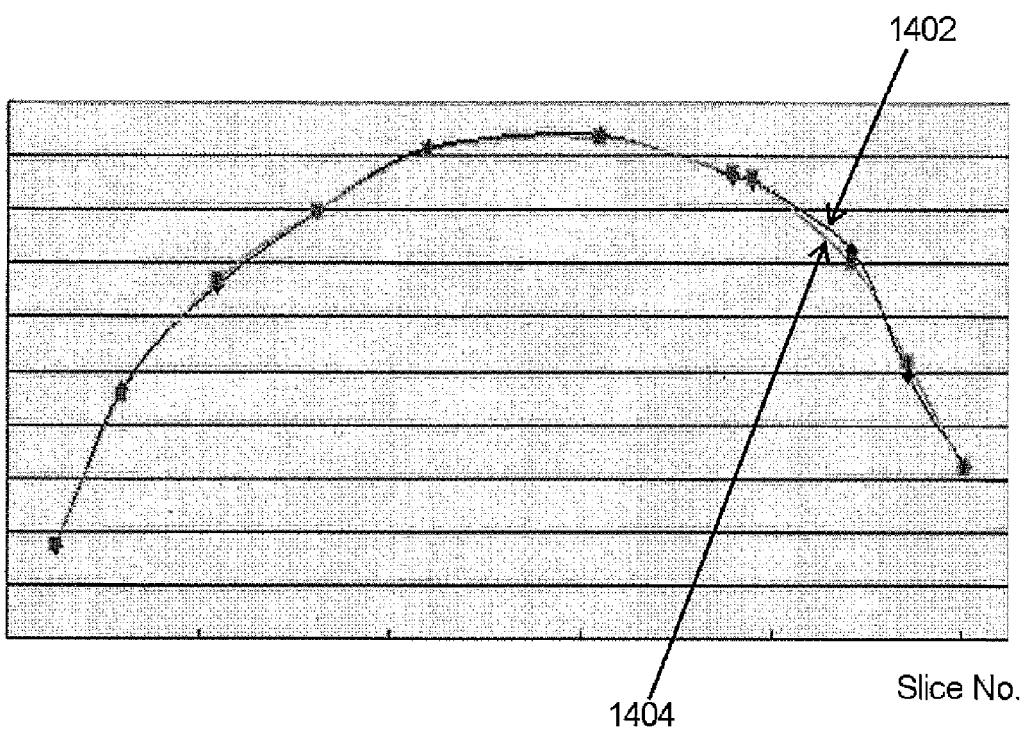
FIG. 14A: an illustration for explaining an example smoothing process applicable in step 1310 of FIG. 14.

FIG. 14A is an illustration for explaining such example smoothing process. In this figure, the horizontal axis is associated with slice No. (short axis slice No.) of the phase-specific myocardial center base point. The vertical axis is associated with the distance between the phase-specific myocardial center base point and the tracing center projected to the slice in which the phase-specific myocardial center base point is included. Black diamonds indicate the phase-specific myocardial center base points determined in step 1308. Line 1402 is the one connecting them. Curve

1404 is created by fitting the original phase-specific myocardial center base points by means of smoothing spline. The gray squires indicates the fitted phase-specific myocardial center base points which have been moved on the basis of the above-mentioned fitting. As can be seen in this figure, the points indicated by the gray squire have smoother transitions in the vertical values with regard to the difference of slice No. It should be noted that the smoothing mentioned above is just one example. The scope of the present invention is not limited by the way of smoothing and the existence of the smoothing operation as mentioned before.

Figure 10:
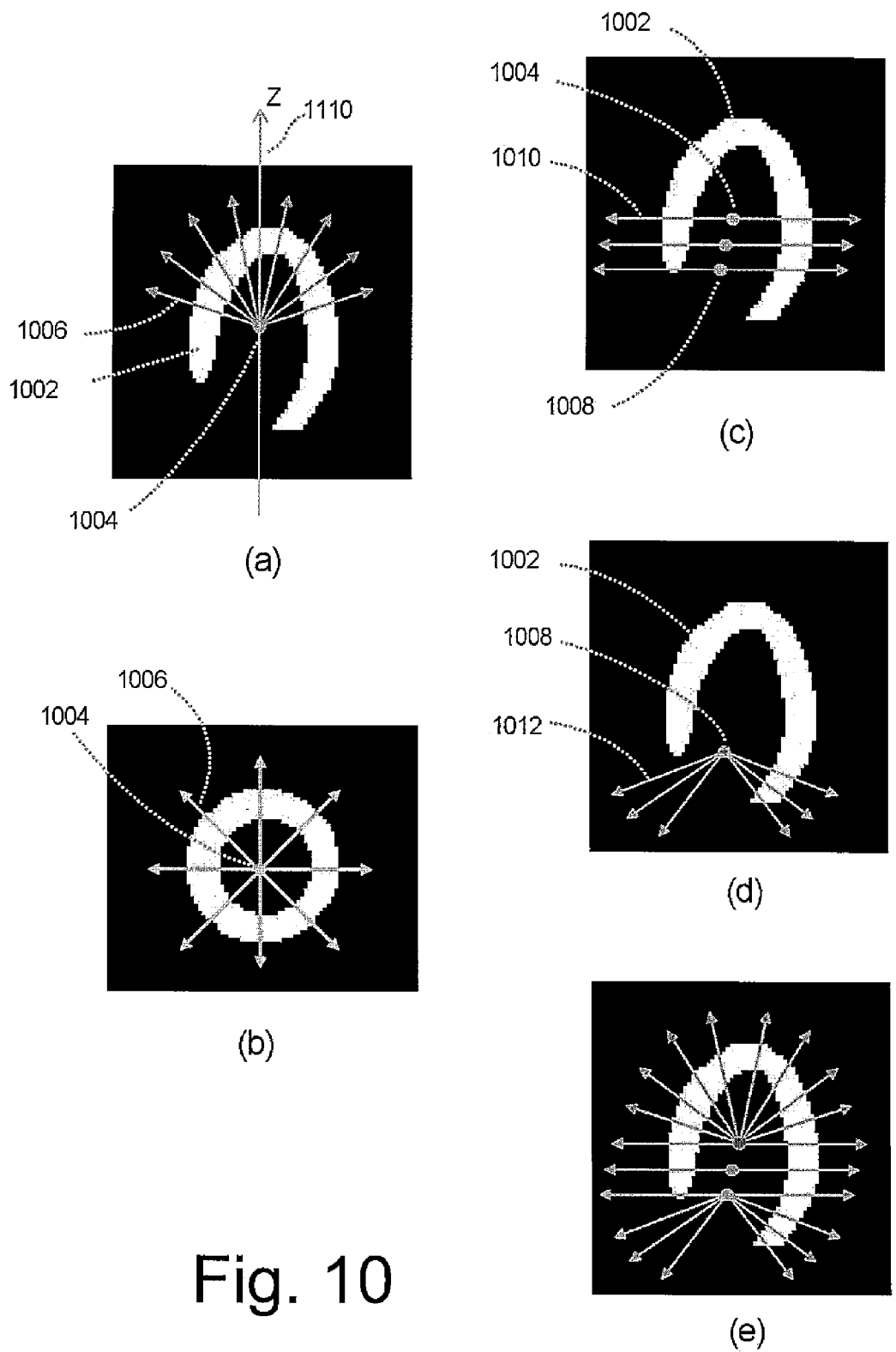
FIG. 10: illustrations for explaining example tracing directions which may be defined in step 912 of FIG. 9.

[2] Smoothing in Conical Plane of which the Central Axis Corresponds to Z-Axis, or Smoothing in a Plane Perpendicular to Z-Axis As explained above, the tracing directions in the above examples were defined by rotating initial tracing directions (having some angles with respect to Z-axis respectively) about Z-axis. As shown in FIG. 10(*b*), an initial tracing direction generated eight final tracing directions by rotating the initial one about Z-axis in 45° step, in the presented example. In this operation, the phase-specific myocardial center base points determined based on the same initial tracing direction are the objects for smoothing. In another word, the phase-specific myocardial center base points determined based on the tracing directions having the same angle with respect to Z-axis and the same tracing center are the objects for smoothing.

Figure 14B:
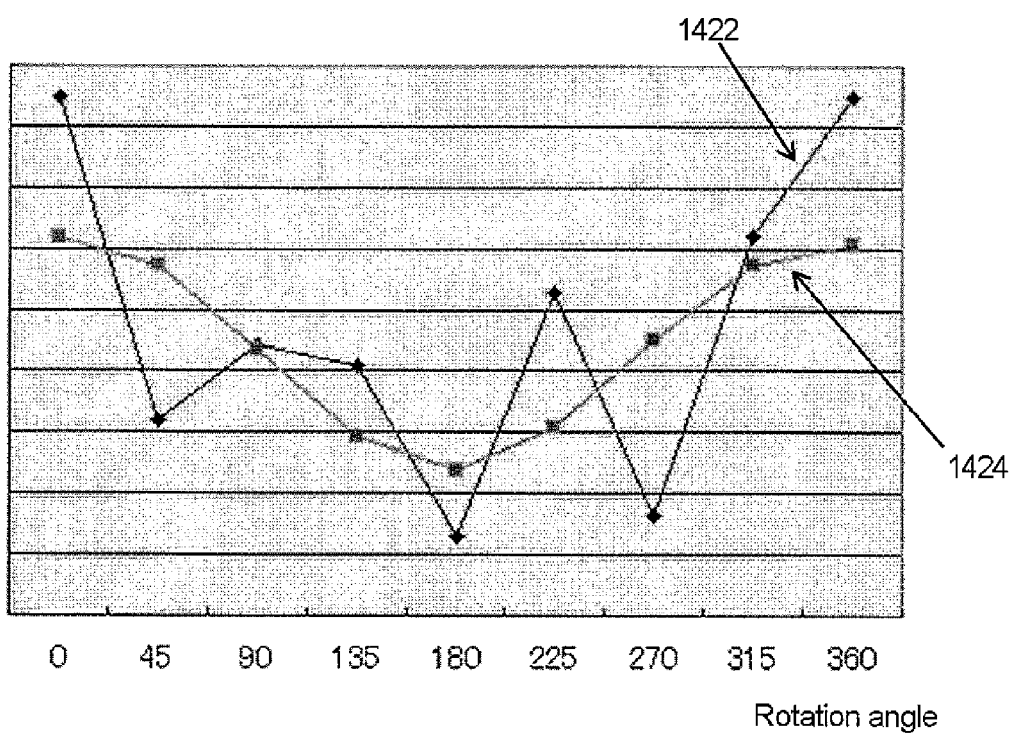
FIG. 14B: an illustration for explaining an example smoothing process applicable in step 1310 of FIG. 14.

FIG. 14B is an illustration for explaining such example smoothing process. In this figure, the horizontal axis is associated with the rotation angle about Z-axis (i.e., rotation angle in a plane perpendicular to Z-axis). The vertical axis is associated with the distance from the tracing center to the phase-specific myocardial center base point. Black diamonds indicate the phase-specific myocardial center base points determined in step 1308. Line 1422 is the one connecting them. Curve 1424 is created by fitting the original phase-specific myocardial center base points by means of Fourier series approximation. The gray squires indicates the fitted phase-specific myocardial center base points which have been moved on the basis of the above-mentioned fitting. As can be seen in this figure, the points indicated by the gray squire have smoother transitions in the vertical values with regard to the difference of rotation angles. It should be noted that the smoothing mentioned above is just one example. The scope of the present invention is not limited by the way of smoothing and the existence of the smoothing operation as mentioned before.

Once the steps 1306-1310 for intra-phase position corrections have been finished for all the phases relating to the process of the present examples, the corrected positions of the phase-specific myocardial center base points are to be further corrected by taking into account the relationships with the other phases.

<Step 1314—Inter-Phase Correction for the Phase-Specific Myocardial Center Base Points>

Figure 15:
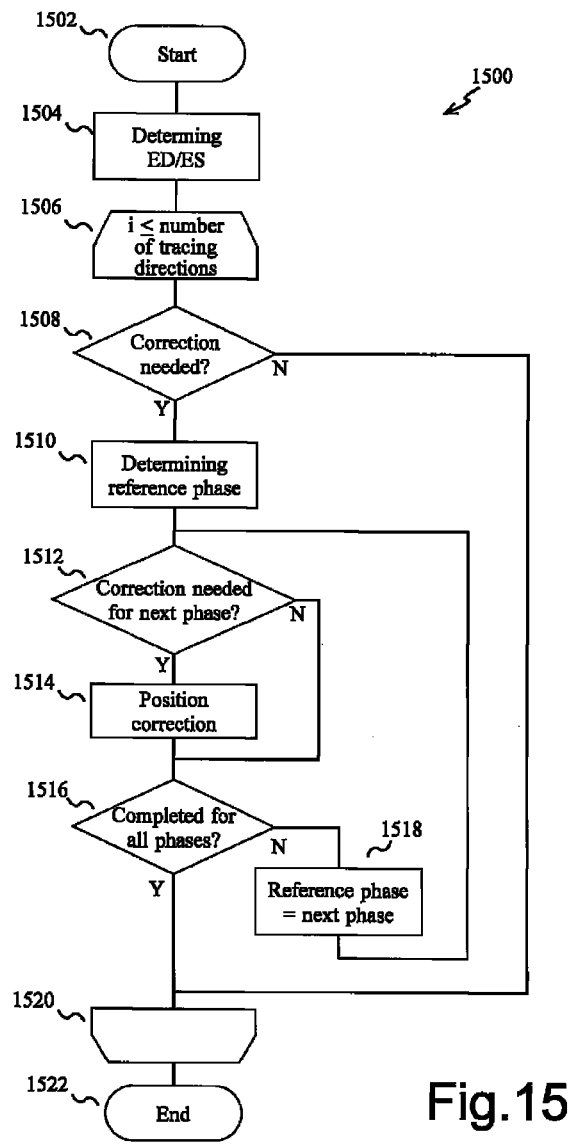
FIG. 15: a flow chart for explaining an example process applicable to step 1314 of FIG. 13.

The inter-phase position correction operation for the phase-specific myocardial center base points will be explained with reference to FIG. 15. This operation can be an example operation performed in step 1314 of FIG. 13. The inter-phase position correction operations of the phase-specific myocardial center base points explained in this step are not essential operations for all of the embodiments of the present invention. However, the smoothing operation provides an advantage that the inter-phase changes of the myocardial contours becomes smoother.

Step 1502 indicates a start of the process. In step 1504, ED (End-Diastole) phase and ES (End-Systole) are determined. They will be a kind of reference in the inter-phase correction. In this example, ED phase and ES phase are determined based on the distances from the tracing center to the phase-specific myocardial center base points.

As mentioned, the presented embodiments have determined phase-specific myocardial center base points for all the phases to be involved in the example processes for all the tracing directions which have been defined for determining the reference myocardial center base points for the summed image data 140. In step 1504, a distance between the phase-specific myocardial center base point and corresponding tracing center is checked for each of these tracing directions, and the phase associated with the longest distance and the phase associated with the shortest distance are identified for each of these tracing directions. Then, the ED phase is determined as the phase which the number of instances identified as associated with the longest distance is larger than the any other phases, and the ES phase is determined as the phase which the number of instances identified as associated with the shortest distance is larger than the any other phases.

In the loop expressed by step 1506 to step 1520, a necessity of position correction is judged for each of the above-mentioned tracing directions. And if it is judged that a position correction may be needed for a certain tracing direction, the position correction operation expressed by steps 1510 to 1518 will be performed for the phase-specific myocardial center base points belonging to that tracing direction.

In step 1508, it is checked that the group of phase-specific myocardial center base points belonging to the tracing direction corresponding to the current loop position satisfies following conditions.

(1) The phase in which the distance between the phase-specific myocardial center base point and the tracing center becomes longest is neither the ED phase nor the phase neighboring to the ED phase.

(2) The phase in which the distance between the phase-specific myocardial center base point and the tracing center becomes shortest is neither the ES phase nor the phase neighboring to the ES phase.

(3) The distance between the phase-specific myocardial center base point and the tracing center does not monotonically decreases from ED to ES (i.e., during the systolic phase), and/or does not monotonically increases from ES to ED (i.e., during the diastole phase).

If the group of phase-specific myocardial center base points belonging to the tracing direction corresponding to the current loop position satisfies any one of the above-mentioned conditions, the process moves to steps 1510 for proceeding position correction operation.

The position correction operation performed in step 1510 and subsequent steps will correct the positions of the phase-specific myocardial center base points such that the transitions of these positions can be regarded as regularly. In step 1510, a reference phase for the position correction operation is determined. This reference phase for correction may be determined in following order of priority.

(1) If the phase in which the distance between the phase-specific myocardial center base point and the tracing center becomes longest is the ED phase, then the ED phase is determined as the reference phase for correction.

(2) If the phase in which the distance between the phase-specific myocardial center base point and the tracing center becomes shortest is the ES phase, then the ES phase is determined as the reference phase for correction.

(3) One of the middle phase in the diastole phase and the middle phase in the systolic phase of which the distance between the phase-specific myocardial center base point and the tracing center is shorter.

The position of the phase-specific myocardial center base point of the reference phase will not be changed during the correction operation.

In step 1512, a necessity of position correction is judged for the phase-specific myocardial center base points of the phase neighboring to the reference phase. This judgment involves a comparison between the distance L1, which is the distance between the phase-specific myocardial center base point and the tracing center of the reference phase, and the distance L2, which is the distance between the phase-specific myocardial center base point and the tracing center of the phase next to the reference phase. If the phase next to the reference phase is in the systolic phase, L1 must be longer than L2. If it is not L1>L2, then the process moves to step 1514 and the position of the phase-specific myocardial center base point of the phase next to the reference phase is corrected so that L2 becomes equal to L1. If the phase next to the reference phase is in the diastole phase, L1 must be shorter than L2. If it is not L1<L2, then the process moves to step 1514 and the position of the phase-specific myocardial center base point of the phase next to the reference phase is corrected so that L2 becomes equal to L1.

In step 1516, it is judged that whether the necessity of position correction has been judged for all the phases with respect to the current tracing direction. If the answer is NO, then the phase for which the necessity of position correction was judged in step 1512 is regarded as the new reference phase for correction, and the process goes back to step 1512 and judges the necessity of position correction for the phase next to the new reference phase.

Figure 16:
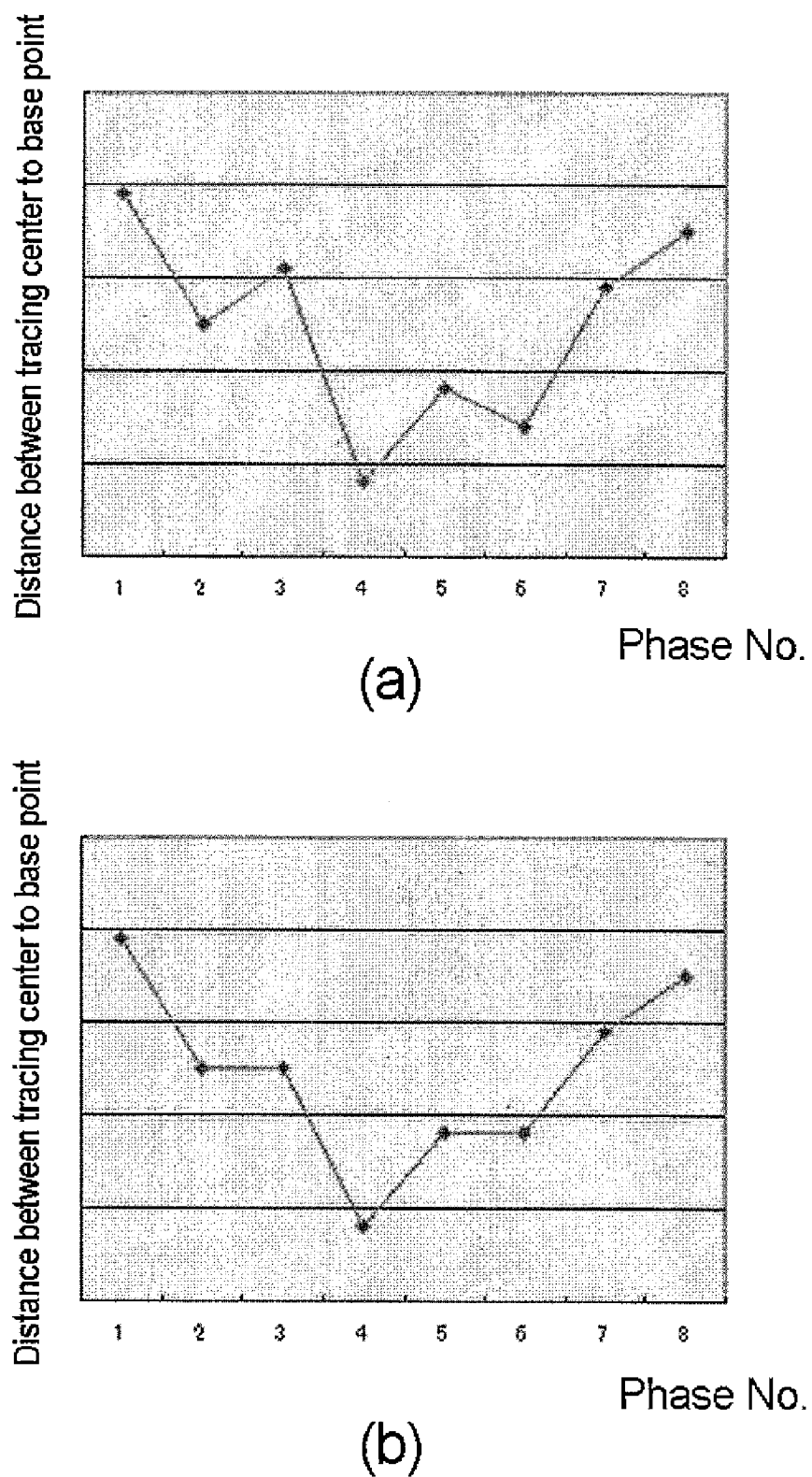
FIG. 16: illustrations for explaining a result of process in step 1514 of FIG. 15

FIG. 16 shows an example of a result of the position correction operation performed in steps 1510-1518 applied for one of the tracing directions. (a) shows the view before the correction and (b) shows the view after the correction. The horizontal axis is associated with identifiers of the phases in the cardiac cycle. These identifiers may be the phase No. Just for example, phase No. 1 is allocated for ED phase and phase No. 4 is allocated for ES phase. The vertical axis is associated with the distance between the phase-specific myocardial center base point and the tracing center. In graph (a), it can be seen that the distance between the phase-specific myocardial center base point and the tracing center is increasing during phase No. 2 and phase No. 3 even this period is the systolic phase. And this distance is decreasing during phase No. 5 and phase No. 6 even the corresponding period is the diastole phase. However, after the correction, this distance does not increase during the systolic phase, and does not decrease during the diastole phase, as can be seen in graph (b). So the determined cardiac muscle does not expand during the systolic phase and does not contract during the diastole phase.

If the operations indicated by steps 1508-1518 are finished for all the tracing directions, the process leaves from the loop and is terminated (step 1522). Now the explanations of the example processes which may be performed in step 170 of FIG. 1B have been completed. In the next section, example processes which may be performed in step 172 of FIG. 1B will be presented.

<Step 172—Determinations of Inner- and Outer-Myocardial Wall Base Points for Each of the Phase Images>

In step 172 of the process shown in FIG. 1B, inner myocardial wall base points and outer myocardial wall base points will be determined for each of the phases based on the reference myocardial center base points, the reference inner myocardial wall base points and the reference outer myocardial wall base points determined for the summed image data 140 in step 168 and the phase-specific myocardial center base points determined for respective phases in step 170. The phase-specific inner- and outer-myocardial wall base points will be determined for respective tracing directions which have been used for determining the reference myocardial center base points and the phase-specific myocardial center base points in steps 168 and 170.

Figure 17:
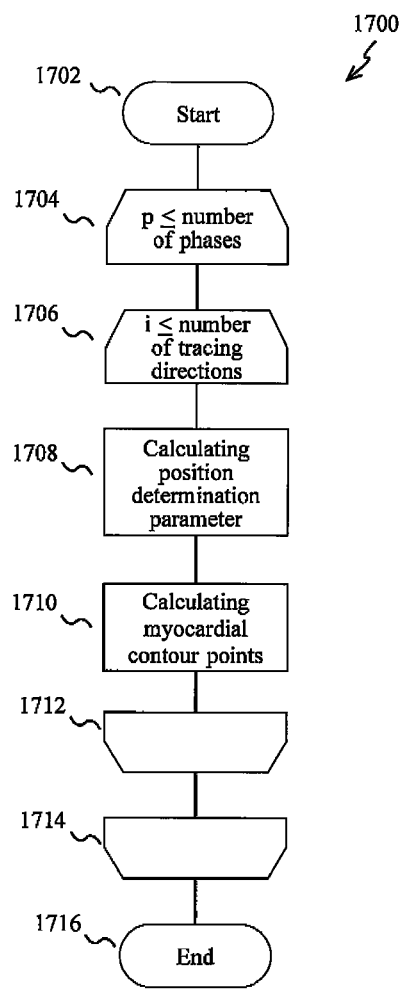
FIG. 17: a flow chart for explaining an example process applicable to step 172 of FIG. 1.

An example process applicable to step 172 of FIG. 1B will be explained with reference to FIG. 17. The loop defined by 1706 and 1712 indicates that an inner- and an outer-myocardial wall base points will be determined for each of the above-mentioned tracing directions. And the loop defined by 1704 and 1714 indicates that the determinations of inner- and outer-myocardial wall base points will be performed for each individual phases. In step 1708, a difference between the reference myocardial center base point and the phase-specific myocardial center base point is calculated for the tracing direction and the phase corresponding to current loop position. The information based on this difference may be called as a 'position determination parameter' in this specification. In step 1710, a phase-specific inner myocardial wall base point and a phase-specific outer myocardial wall base point are determined for the current tracing direction of the current phase by moving the reference inner myocardial wall base point and the reference outer myocardial wall base point associated with the current phase and the tracing direction based on the position determination parameter.

In one embodiment, the position determination parameter may have a value larger than said difference between the reference myocardial center base point and the phase-specific myocardial center base point. For example, the value of the position determination parameter may be 1.7*said difference.

In one embodiment, the amount of movement of the reference inner myocardial wall base point may be larger than the amount of movement of the reference outer myocardial wall base point. In one embodiment, the amount of movement of the reference inner myocardial wall base point may be 0.7*said position determination parameter, and the amount of morphology of the reference outer myocardial wall base point may be 0.3*said position determination parameter.

In one embodiment, the position determination parameter may be a component having a direction such as a vector. For example, it may be expressed as D=(dx, dy, dz), where D is the position determination parameter. For example, suppose that the reference myocardial center base point $R_0$ may be expressed as $R_0=(r_0x, r_0y, r_0z)$ and the phase-specific myocardial center base point $P_0$ may be expressed as $P_0=(p_0x, p_0y, p_0z)$. Then, the position determination parameter D may be expressed as $D=1.7*(R_0-P_0)$, i.e., $(dx, dy, dz)=1.7*\{(r_0x, r_0y, r_0z)-(p_0x, p_0y, p_0z)\}$. Further, suppose that the reference inner myocardial wall base point $R_1$ may be expressed as $R_1(r_1x, r_1y, r_1z)$, the reference outer myocardial wall base point $R_2$ may be expressed as $R_2=(r_2x, r_2y, r_2z)$, phase-specific inner myocardial wall base point $P_1$ may be expressed as $P_1=(p_1x, p_1y, p_1z)$, and the phase-specific outer myocardial wall base point $P_2$ may be expressed as $P_2=(p_2x, p_1y, p_2z)$. Then P1=R1−0.7D, and P2=0.3D, i.e., $(p_1x, p_1y, p_1z)=(r_1x, r_1y, r_1z)\ 0.7(dx, dy, dz)$ and $(p_2x, P_2y, p_2z)=(r_2x, r_2y, r_2z)-0.3(dx, dy, dz)$, for example, in one embodiment.

Figure 18:
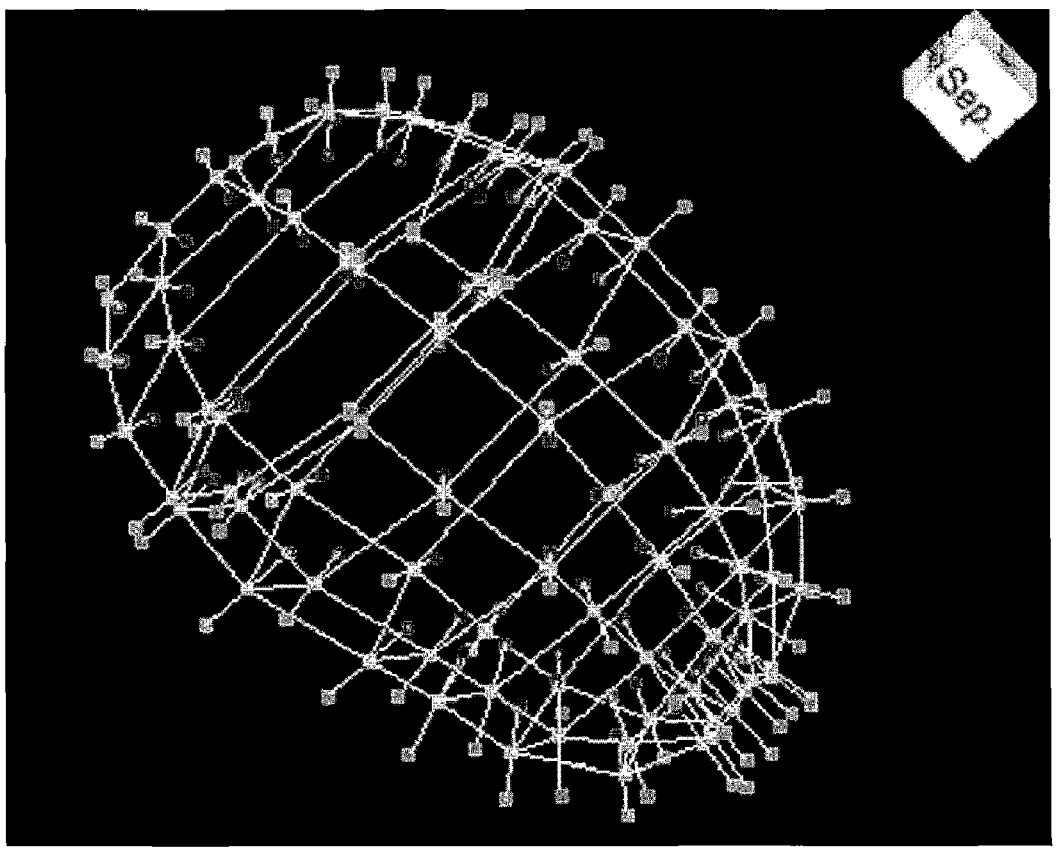
FIG. 18: an illustration for showing examples of myocardial center base points, inner myocardial wall base points and outer myocardial wall base points determined after the completion of process 160 of FIG. 1B.

If the determinations of the phase-specific inner- and outer-myocardial wall base points have been completed for all the tracing directions and for all the relevant phases, the process exits the loops and will be terminated (step 1716). Just for an example, FIG. 18 shows an image of myocardial center base points, inner myocardial wall base points and outer myocardial wall base points determined for a certain phase. In this picture, the phase-specific myocardial center base points are connected by line.

Now the process 160 illustrated in FIG. 1B has been completed. The process 160 determines the myocardial contour base points of respective phase data based on a summed image data created by summing those phase data. Hence, the process 160 provides smooth changes of myocardial contour base points in phase.

Various examples have been disclosed with respect to the process 160 illustrated in FIG. 1B. However, it should be noted that these disclosures are merely examples and the embodiments of the process 160 are not limited to those disclosed in the present description and/or the drawings. Some of the present steps may not be essential steps for all of the embodiments of the present invention. The orders of steps may be changed in the other various embodiments. In some embodiments, two or more of the disclosed steps may be combined to a single step and performed integrally. In some embodiments, some of the discloses single steps may be divided into two or three substeps and performed sequentially or in parallel. The image data processed in the presented examples are the ones obtained from a SPECT system. But the present invention can also be applied to the image data obtained from PET systems. The target set of image data in the above examples comprises eight image data associated different phases. But the present invention can also be applied for the other sets of images comprising different number of image data (of different phases), such as 4 or 17. The process 160 is also of course just one example of the embodiments of the present invention. There are huge varieties in the embodiments the present invention.

The number of the determined myocardial wall points may not be so many, at the stage where the process 160 is just finished. As can be seen in FIG. 18, the inner- and the outer-myocardial wall base points were merely determined sparsely for the each phase image in the above-mentioned examples. Hence, there may be a need to determine the inner- and the outer-myocardial wall points more densely. In one example, an interpolation process may be employed such that all the (short axis) slices located between the ventricle apex and the ventricle base have at least one inner myocardial wall point and/or at least one outer myocardial wall point. It is possible to employ any types of interpolation techniques for such process. Since the inner- and outer-myocardial wall base points have been determined such that their locations are changed smoothly with respect to the phase changes, the locations of the interpolated points will also be changed more smoothly with respect to the phase changes than the existing technologies.

The present application further discloses a novel technique for interpolating myocardial inner and outer-wall points into slices. This technique comprises a stage of interpolation in planes parallel to Z-axis and a stage of interpolation in planes perpendicular to Z-axis. An example of implementation of this technique will be explained below with reference to FIG. 19A to FIG. 19C.

<Interpolation in Planes Parallel to Z-Axis>

Figure 19A:
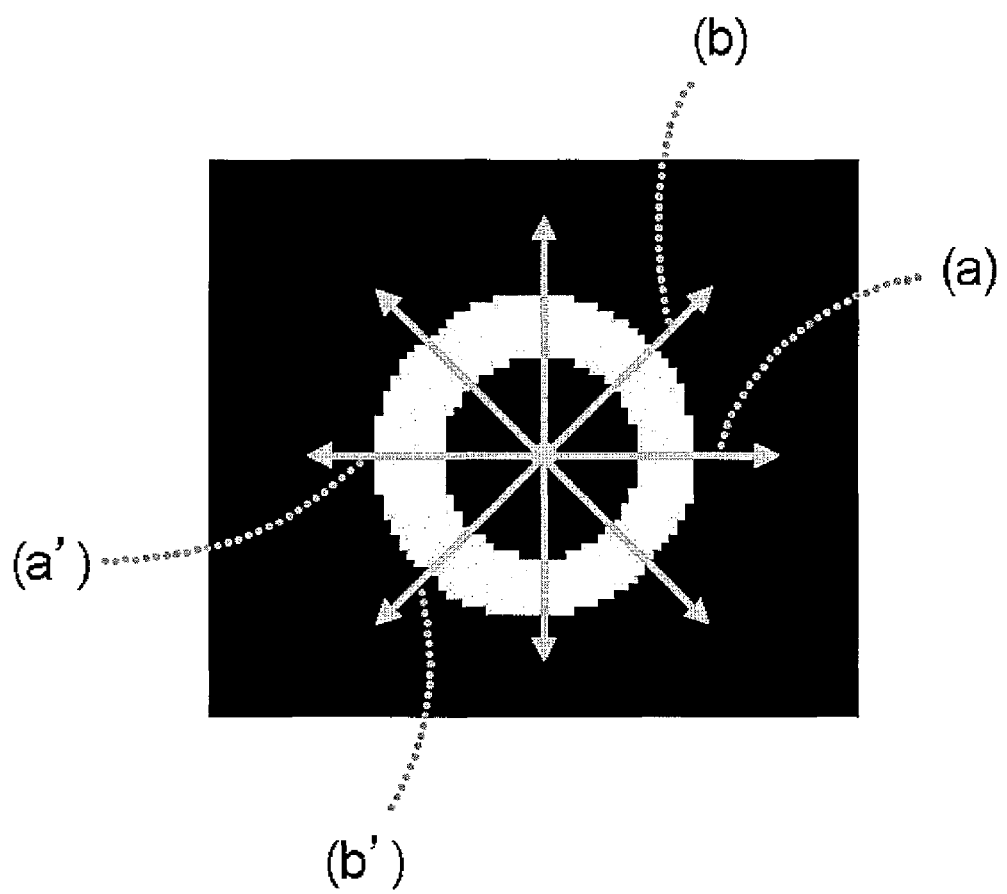
FIG. 19A: an illustration for explaining an example interpolation process for inner- and outer-myocardial wall points of individual slice.

FIG. 19A is the same figure as FIG. 10(*b*). As explained before in connection with FIGS. 10(*a*) to 10(*e*), the process 160 defines tracing directions around Z-axis in a predetermined step (which was 45°) for the determinations of the myocardial contour base points, as can also be seen in FIG. 19A as a manner projected to a plane perpendicular to Z-axis. Please note that Z-axis has been defined as an axis passing through the tracing center and being perpendicular to the short axis slices. The interpolation explained in this section is performed based on the group having the same rotation angle with respect to Z-axis. For example, the difference of rotation angles about Z-axis between the directions (a) and (a') in FIG. 19A is 180°. Thus the phase-specific inner- and outer-myocardial wall points determined in the tracing directions which can be projected to the directions (a) and (a') can be regarded as being included in the same plane. And the interpolation explained in this section is performed for a group of these phase-specific inner- and outer-myocardial wall points regarded as included in the same plane. Similarly, the difference of rotation angles about Z-axis between the directions (b) and (b') in FIG. 19A is 180°. Thus the phase-specific myocardial wall points determined in the tracing directions which can be projected as (b) and (b') can be regarded as being included in the same plane. And the myocardial wall points included in this plane will be an object of interpolation operation explained in this section. In the example of FIG. 19A, there are four plans having different rotation angles with respect to Z-axis. The interpolation operation of this section will be performed in connection with each of these four planes.

It should be noted that the original points of Z-axes used in apical region, center region and basal region are different as mentioned above in connection with steps 912, 916 and 920 and FIG. 10(*e*). However, since these Z-axes are all parallel, the differences of the original points are ignored and only the rotation angles about Z-axes are taken into account. Accordingly, the interpolation operation explained in this section is applied for a set of phase-specific myocardial inner- and outer-wall points having the same and 180° different rotation angles about Z-axis regardless of the differences of the tracing center.

Figure 19B:
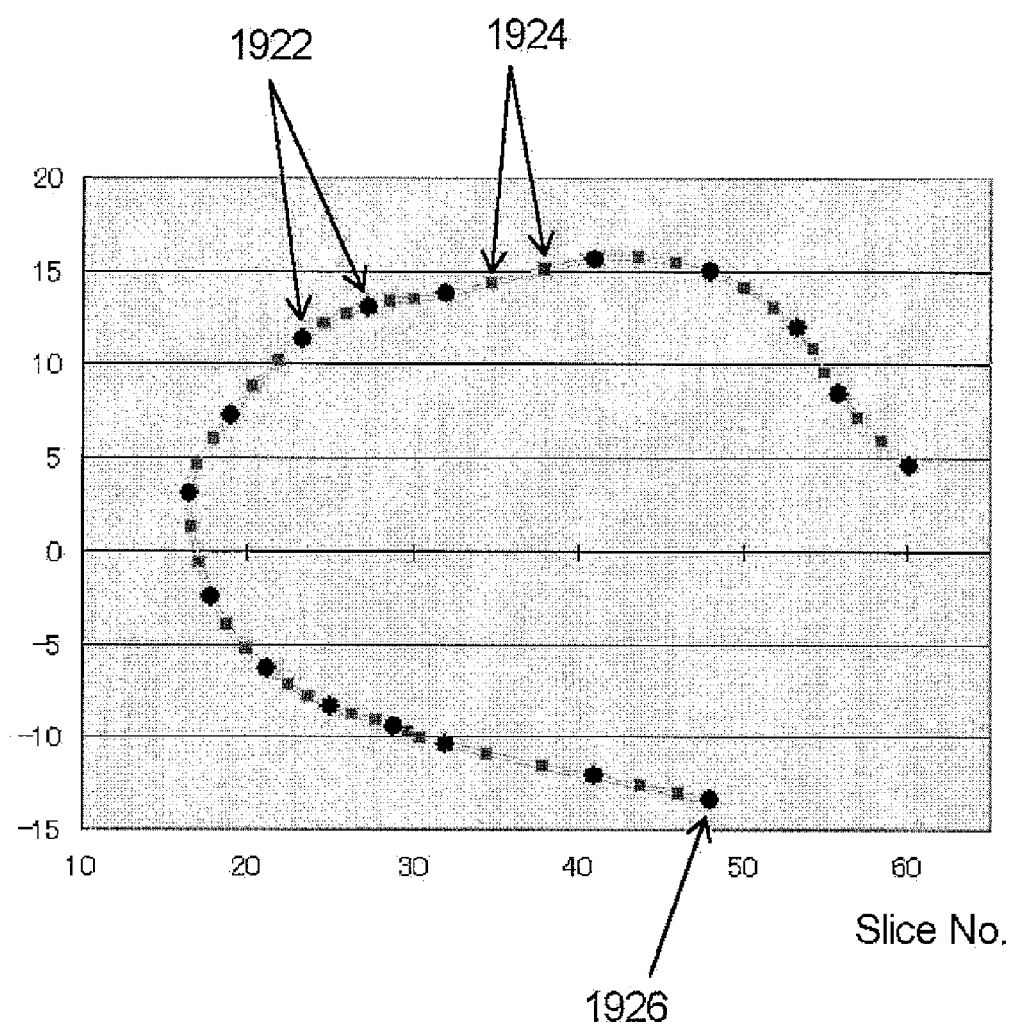
FIG. 19B: an illustration for explaining an example interpolation process for inner- and outer-myocardial wall points of individual slice.

FIG. 19B is provided for explaining the interpolation disclosed in this section performed in a plane parallel to Z-axis. All of the illustrated data points are associated with the same or 180° different rotation angles with respect to Z-axis and the same phase. In this figure, the black solid circles 1922 indicate outer myocardial wall base points determined for a certain phase by step 160. The horizontal axis is associated with the slice No. of the short axis slice. The value associated with the vertical axis is a distance between an outer myocardial wall base point and a tracing center that is projected to a short axis slice in which the corresponding outer myocardial wall base point is included. The outer myocardial wall base points shown in FIG. 19B are associated with one of the two rotation angles about Z-axis with 180° difference, as can be understood from FIG. 19A (see (a) and (a'), or (b) and (b')). The outer myocardial wall base points having positive vertical values in FIG. 19B are associated with one of these rotation angles (i.e., associated with, e.g., (a) or (b)), the points having negative vertical values are associated with the other one of these rotation angles (i.e., associated with, e.g., (a') or (b')). In FIG. 19B, the gray solid squires 1924 indicate outer myocardial wall points determined by means of spline interpolation of the outer myocardial wall base points. The number of interpolated points illustrated in this figure is not so many. But it is just because of limitations in drawing. Actually, the interpolation operation is performed so that each of the short axis slices existed between the apical edge and the basal edge of the ventricle preferably have two outer myocardial wall points (one is above the horizontal axis and the other is below the horizontal axis). Please note that it is not mandatory that each of the slices have two outer myocardial wall points. For example, the lower myocardial wall points are missing at slices No. 50-60. It is because the corresponding portion of the ventricle base is not continuous. However, in some embodiments, temporary wall points may be defined for lower side of slices No. 50-60 for the convenience of the interpolation performed in the next stage (interpolation in planes perpendicular to Z-axis). In some embodiments, the temporary wall points may be the same point as the last effective wall point (1926) in the short axis slice. The inner myocardial wall points may also be determined by the same interpolation operation.

<Interpolation in Planes Perpendicular to Z-Axis>

Figure 19C:
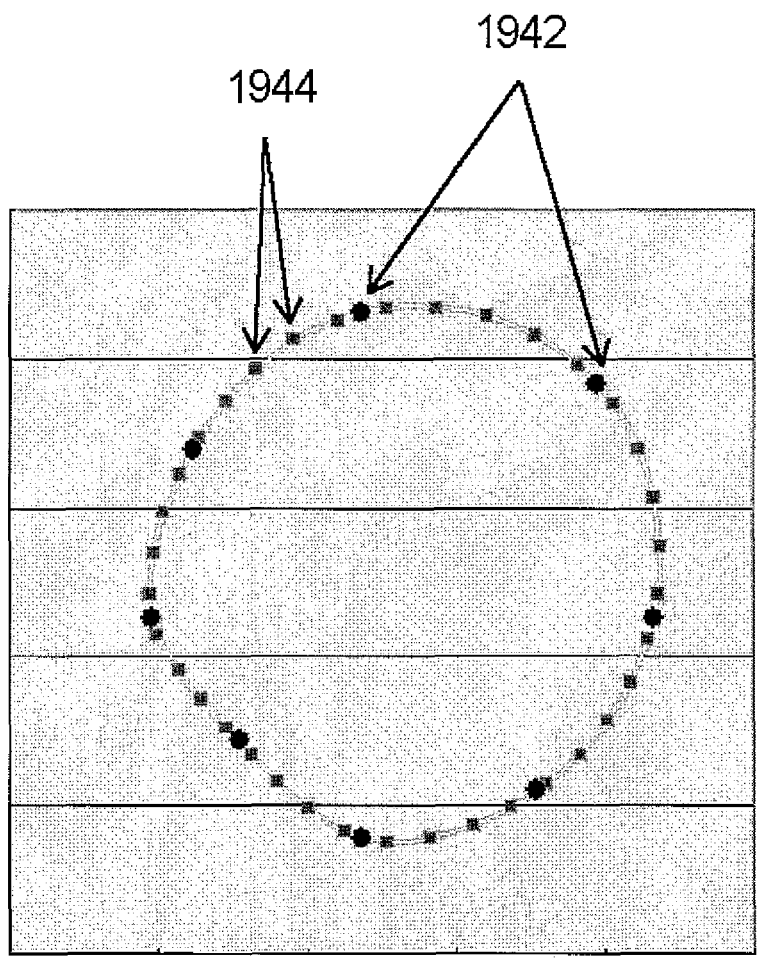
FIG. 19C: an illustration for explaining an example interpolation process for inner- and outer-myocardial wall points of individual slice.

An example of the interpolation operation performed in a short axis slice (i.e., a plane perpendicular to Z-axis) will now be explained with reference to FIG. 19C. In this figure, the black solid circles 1942 indicate outer myocardial wall base points determined for a certain phase by step 160 or interpolated outer myocardial wall points created by the interpolation operation performed in plane parallel to Z-axis as presented in the last section. The gray solid squires 1944 indicate interpolated outer myocardial wall points determined by means of spline interpolation of the points 1942. In this example, the spline interpolation is performed so that one interpolated outer myocardial wall point is provided in each 10°, where the basis of angle is a ventricle center of the relevant slice (i.e., ventricle center determined in step 324 in the current slice). The inner myocardial wall points are also determined by the same interpolation operation.

The above-mentioned processes enable to determine inner- and/or outer myocardial wall points for all slices including myocardium for each of the phase image data (e.g., each of image data 131-138).

<Presentation of Inner- and Outer-Myocardial Wall Points>

Figure 20:
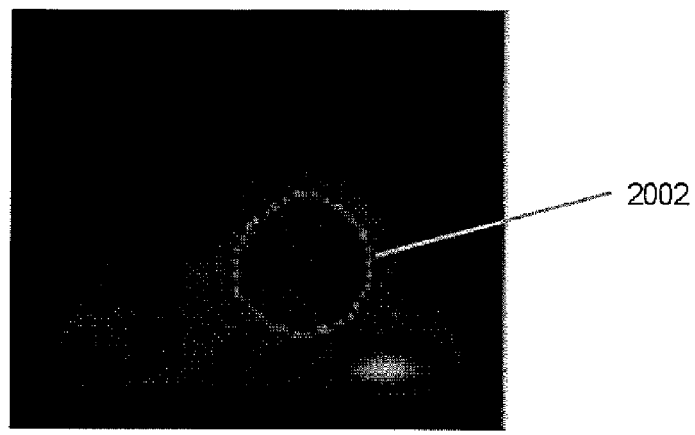
FIG. 20: illustrations for explaining examples ways for displaying determined inner- and outer-myocardial wall points of individual slice.
Figure 20:
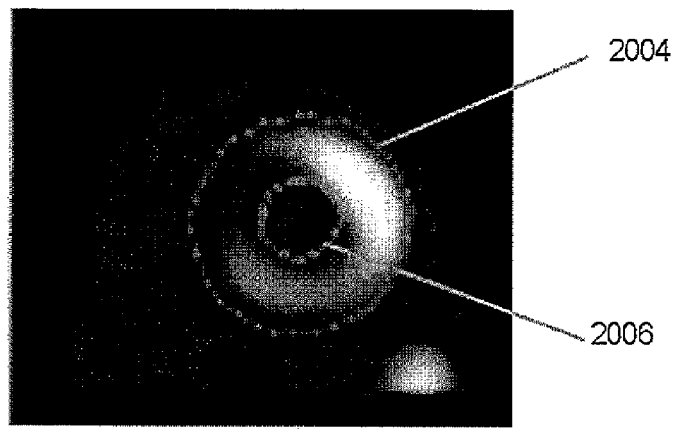
Figure 20:
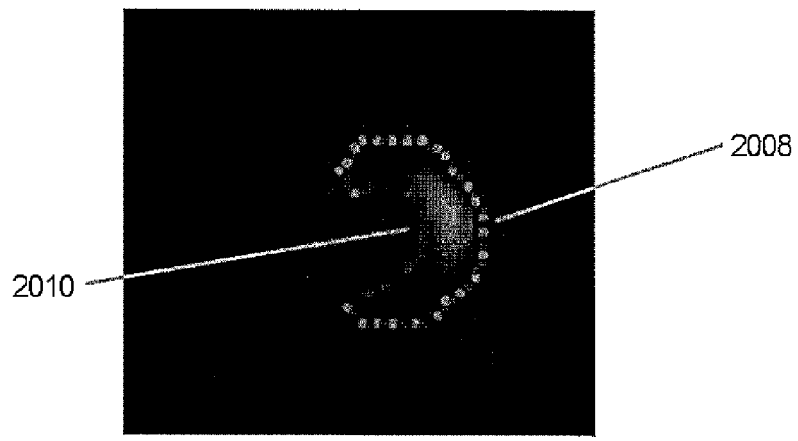

In this section, an example for presenting the determined inner- and outer-myocardial wall points will be explained with reference to FIG. 20. FIG. 20(*a*) is an example of presentation of myocardial contour points in an apical region. (b) is an presentation example of myocardial contour points in a central region, and (c) is a presentation example of myocardial contour points in a basal region. As can be seen in these figures, they are short axis images.

In each of the short axis slices, if the angle of discontinuity of the outer myocardial wall points is less than 20° (where the basis of angle is a ventricle center, e.g., the ventricle center determined in step 324 in the current slice), then the outer myocardial wall points are connected each other for creating a closed curve that is to be presented as an outer myocardial contour, as can be seen in (a) and (b). Similarly, if the angle of discontinuity of the inner myocardial wall points is less than 20°, then the inner myocardial wall points are connected each other for creating a closed curve that is to be presented as a inner myocardial contour, as can be seen in (b). If both the angle of discontinuity of the inner myocardial wall points and the angle of discontinuity of the outer myocardial wall points are equal or greater than 20°, then the largest continuous region of the outer wall points and the largest continuous region of the inner wall points are connected, and the formed closed curve that will be presented as a myocardial contour, as can be seen in (c).

Some examples of the preferred embodiments of the present invention have now been explained. It should be noted that the reason why these examples are provided is not to limit a scope of invention; the reason is to satisfy the requirement of the patent law and to be used for understanding and practicing the present invention. The present invention can be embodied in many different ways. There are a lot of variations for the embodiments of the present invention. Individual features included in the presented various examples may be used for various other embodiments and implementations in combination regardless of they are disclosed explicitly or not in the present specification; those individual features are not exclusive to the constructions explicitly presented as including those features. The orders flow charts are just examples and not mandatory. Some steps in these flow charts can be implemented in different orders, executed in parallel or executed simultaneously. These variations are all included in the scope of the present invention. It should also be noted that the order of writing of claim components may not be corresponding to the actual execution steps for all the possible embodiments. The scopes of claims cover the embodiments with different orders. It should be noted that the applicant claims rights to obtain patents for all the embodiments which do not exceed the spirit of the present invention, regardless whether those embodiments are included in the current set of claims or not.

The invention claimed is:

1. A method performed by a computer processing unit executing computer readable instructions, stored in a non-transitory computer-readable memory, comprising:
   (a) creating a summed 3D nuclear medicine imaging data by summing a plurality of 3D nuclear medicine imaging data pixel by pixel, wherein each of the plurality of 3D nuclear medicine imaging data is associated with a plurality of different phases of a cardiac cycle;
   (b) determining pixels corresponding to myocardial regions in the summed 3D nuclear medicine imaging data;
   (c) defining a plurality of tracing directions based on the summed 3D nuclear medicine imaging data, and determining a reference myocardial center base point, a reference inner myocardial wall base point and a reference outer myocardial wall base point for each tracing direction of the plurality of tracing directions;
   (d) determining a phase-specific myocardial center base point for each tracing direction of the plurality of tracing directions for each phase of the plurality of different phases based on the corresponding 3D nuclear medicine imaging data; and
   (e) determining a difference in position of the reference myocardial center base point and the phase-specific myocardial center base point, and determining a phase-specific inner myocardial wall base point and a phase-specific outer myocardial wall base point by shifting the reference inner myocardial wall base point and the reference outer myocardial wall base point respectively based on the determined difference, for each tracing direction of the plurality of tracing directions for each phase of the plurality of different phases.

2. The method of claim 1, wherein creating a summed 3D nuclear medicine imaging data in said step (a) being performed after applying a position adjustment operation for at least some of said 3D nuclear medicine imaging data.

3. The method of claim 1, wherein said step (c) further comprises:
   creating a binary image data by assigning a first value to pixels in the summed 3D nuclear medicine imaging data which are determined as being associated with myocardial regions, and assigning a second value to pixels in the summed 3D nuclear medicine imaging data which are determined as not being associated with myocardial regions; and
   determining the reference myocardial center base point, the reference inner myocardial wall base point and the reference outer myocardial wall base point based on said binary image data in each tracing direction of the plurality of tracing directions.

4. The method of claim 1, wherein said plurality of tracing directions defined in said step (c) are defined such that:
for a region located on an apical side, tracing directions are defined as radially and three-dimensionally from a predetermined starting point in a cardiac ventricle;
for a region located on a basal side, tracing directions are also defined as radially and three-dimensionally from a different starting point in a cardiac ventricle; and
for a central myocardial region located between the region located on the apical side and the region located on the basal side, tracing directions are defined as radially and two-dimensionally in a short axial plane.

5. The method of claim 1, wherein said step (d) is performed such that the phase-specific myocardial center base point may be determined based not only on the 3D nuclear medicine imaging data of the corresponding phase, but also on the 3D nuclear medicine imaging data of the neighboring phases.

6. The method of claim 1, wherein an inter-slice correction and/or an intra-slice correction are applied to positions of at least some of the phase-specific myocardial center base points, before determining the phase-specific inner myocardial wall base points and/or the phase-specific outer myocardial wall base points.

7. The method of claim 1, wherein an inter-phase correction is applied to positions of at least some of the phase-specific myocardial center base points, before determining the phase-specific inner myocardial wall base points and phase-specific outer myocardial wall base points.

8. The method of claim 1, wherein an amount of shifting of inner myocardial wall base points is greater than an amount of shifting of outer myocardial wall base points.

9. An apparatus comprising at least one processor and at least one memory including computer program code, wherein the at least one memory and the computer code are configured, with the at least one processor, to cause the apparatus to at least perform the following:
(a) creating a summed 3D nuclear medicine imaging data by summing a plurality of 3D nuclear medicine imaging data pixel by pixel, wherein each of the plurality of 3D nuclear medicine imaging data is associated with a plurality of different phases of a cardiac cycle;
(b) determining pixels corresponding to myocardial regions in the summed 3D nuclear medicine imaging data;
(c) defining a plurality of tracing directions based on the summed 3D nuclear medicine imaging data, and determining a reference myocardial center base point, a reference inner myocardial wall base point and a reference outer myocardial wall base point for each tracing direction of the plurality of tracing directions;
(d) determining a phase-specific myocardial center base point for each tracing direction of the plurality of tracing directions for each phase of the plurality of different phases based on the corresponding 3D nuclear medicine imaging data; and
(e) determining a difference in position of the reference myocardial center base point and the phase-specific myocardial center base point, and determining a phase-specific inner myocardial wall base point and a phase-specific outer myocardial wall base point by shifting the reference inner myocardial wall base point and the reference outer myocardial wall base point respectively based on the determined difference, for each tracing direction of the plurality of tracing directions for each phase of the plurality of different phases.

10. The apparatus of claim 9, wherein creating a summed 3D nuclear medicine imaging data in said step (a) being performed after applying a position adjustment operation for at least some of said 3D nuclear medicine imaging data.

11. The apparatus of claim 9, wherein said step (c) further comprises:
creating a binary image data by assigning a first value to pixels in the summed 3D nuclear medicine imaging data which are determined as being associated with myocardial regions, and assigning a second value to pixels in the summed 3D nuclear medicine imaging data which are determined as not being associated with myocardial regions; and
determining the reference myocardial center base point, the reference inner myocardial wall base point and the reference outer myocardial wall base point based on said binary image data in each tracing direction of the plurality of tracing directions.

12. The apparatus of claim 9, wherein said plurality of tracing directions defined in said step (c) are defined such that:
for a region located on an apical side, tracing directions are defined as radially and three-dimensionally from a predetermined starting point in a cardiac ventricle;
for a region located on a basal side, tracing directions are also defined as radially and three-dimensionally from a different starting point in a cardiac ventricle; and
for a central myocardial region located between the region located on the apical side and the region located on the basal side, tracing directions are defined as radially and two-dimensionally in a short axial plane.

13. The apparatus of claim 9, wherein said step (d) is performed such that the phase-specific myocardial center base point may be determined based not only on the 3D nuclear medicine imaging data of the corresponding phase, but also on the 3D nuclear medicine imaging data of the neighboring phases.

14. The apparatus of claim 9, wherein an inter-slice correction and/or an intra-slice correction are applied to positions of at least some of the phase-specific myocardial center base points, before determining the phase-specific inner myocardial wall base points and/or the phase-specific outer myocardial wall base points.

15. The apparatus of claim 9, wherein an inter-phase correction is applied to positions of at least some of the phase-specific myocardial center base points, before determining the phase-specific inner myocardial wall base points and phase-specific outer myocardial wall base points.

16. The apparatus of claim 9, wherein an amount of shifting of inner myocardial wall base points is greater than an amount of shifting of outer myocardial wall base points.

17. A computer program product embodied on a non-transitory computer-readable medium in which a computer program is stored that, when being executed by a computer, is configured to provide instructions to control or carry out:
(a) creating a summed 3D nuclear medicine imaging data by summing a plurality of 3D nuclear medicine imaging data pixel by pixel, wherein each of the plurality of 3D nuclear medicine imaging data is associated with a plurality of different phases of a cardiac cycle;
(b) determining pixels corresponding to myocardial regions in the summed 3D nuclear medicine imaging data;
(c) defining a plurality of tracing directions based on the summed 3D nuclear medicine imaging data, and determining a reference myocardial center base point, a reference inner myocardial wall base point and a reference outer myocardial wall base point for each tracing direction of the plurality of tracing directions;

(d) determining a phase-specific myocardial center base point for each tracing direction of the plurality of tracing directions for each phase of the plurality of different phases based on the corresponding 3D nuclear medicine imaging data; and (e) determining a difference in position of the reference myocardial center base point and the phase-specific myocardial center base point, and determining a phase-specific inner myocardial wall base point and a phase-specific outer myocardial wall base point by shifting the reference inner myocardial wall base point and the reference outer myocardial wall base point respectively based on the determined difference, for each tracing direction of the plurality of tracing directions for each phase of the plurality of different phases.

18. The computer program product of claim 17, wherein creating a summed 3D nuclear medicine imaging data in said step (a) being performed after applying a position adjustment operation for at least some of said 3D nuclear medicine imaging data.

19. The computer program product of claim 17, wherein said step (c) further comprises:
creating a binary image data by assigning a first value to pixels in the summed 3D nuclear medicine imaging data which are determined as being associated with myocardial regions, and assigning a second value to pixels in the summed 3D nuclear medicine imaging data which are determined as not being associated with myocardial regions; and
determining the reference myocardial center base point, the reference inner myocardial wall base point and the reference outer myocardial wall base point based on said binary image data in each tracing direction of the plurality of tracing directions.

20. The computer program product of claim 17, wherein said plurality of tracing directions defined in said step (c) are defined such that:
for a region located on an apical side, tracing directions are defined as radially and three-dimensionally from a predetermined starting point in a cardiac ventricle;
for a region located on a basal side, tracing directions are also defined as radially and three-dimensionally from a different starting point in a cardiac ventricle; and
for a central myocardial region located between the region located on the apical side and the region located on the basal side, tracing directions are defined as radially and two-dimensionally in a short axial plane.

21. The computer program product of claim 17, wherein said step (d) is performed such that the phase-specific myocardial center base point may be determined based not only on the 3D nuclear medicine imaging data of the corresponding phase, but also on the 3D nuclear medicine imaging data of the neighboring phases.

22. The computer program product of claim 17, wherein an inter-slice correction and/or an intra-slice correction are applied to positions of at least some of the phase-specific myocardial center base points, before determining the phase-specific inner myocardial wall base points and/or the phase-specific outer myocardial wall base points.

23. The computer program product of claim 17, wherein an inter-phase correction is applied to positions of at least some of the phase-specific myocardial center base points, before determining the phase-specific inner myocardial wall base points and phase-specific outer myocardial wall base points.

24. The computer program product of claim 17, wherein an amount of shifting of inner myocardial wall base points is greater than an amount of shifting of outer myocardial wall base points.

* * * * *